United States Patent
Saint et al.

(10) Patent No.: US 11,484,657 B2
(45) Date of Patent: Nov. 1, 2022

(54) INTELLIGENT MEDICATION DELIVERY SYSTEMS AND METHODS

(71) Applicant: Companion Medical, Inc., San Diego, CA (US)

(72) Inventors: Sean Saint, San Diego, CA (US); Mike Mensinger, San Diego, CA (US); Arnold Holmquist, San Diego, CA (US); Jack Pryor, San Diego, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 134 days.

(21) Appl. No.: 16/004,275

(22) Filed: Jun. 8, 2018

(65) Prior Publication Data

US 2018/0353698 A1   Dec. 13, 2018

Related U.S. Application Data

(60) Provisional application No. 62/517,819, filed on Jun. 9, 2017.

(51) Int. Cl.
*A61M 5/20* (2006.01)
*A61M 5/315* (2006.01)
(Continued)

(52) U.S. Cl.
CPC .......... *A61M 5/31546* (2013.01); *A61M 5/20* (2013.01); *A61M 5/24* (2013.01);
(Continued)

(58) Field of Classification Search
CPC .. G06T 1/00; G06K 9/36; G06F 19/00; G06N 99/00; A61M 5/1723; A61M 2205/52;
(Continued)

(56) References Cited

U.S. PATENT DOCUMENTS

| 4,498,904 A | 2/1985 | Turner et al. |
| 4,515,584 A | 5/1985 | Abe et al. |

(Continued)

FOREIGN PATENT DOCUMENTS

| CA | 2963672 A1 | 4/2016 |
| EP | 0298067 | 4/1989 |

(Continued)

OTHER PUBLICATIONS

Cision PR News Wire, "CompaNion Medical Announces Insights by InPen, the Future of MDI Reports", Jun. 20, 2018.
(Continued)

*Primary Examiner* — Rebecca E Eisenberg
*Assistant Examiner* — Anna E Goldberg-Richmeier
(74) *Attorney, Agent, or Firm* — Carter, DeLuca & Farrell LLP

(57) ABSTRACT

Systems, devices, and techniques are disclosed for administering and tracking medicine to patients and providing health management capabilities for patients and caregivers. In some aspects, a system includes an injection pen device including a dose setting mechanism, a dispensing mechanism, and an electronics unit to generate dose data associated with a dispensing event of a dose of the medicine dispensed from the injection pen device and time data associated with the dispensing event; a mobile device in wireless communication to receive and process the dose data; and a software application configured to determine a recommended dose based on health data and contextual data associated with a user of the injection pen device, the software application including a learning dose calculator module to adaptively calculate the recommended dose of the medicine based on time-relevant and circumstances-relevant data specific to the user of the injection pen device.

20 Claims, 20 Drawing Sheets

(51) Int. Cl.

| | | |
|---|---|---|
| *A61M 5/34* | (2006.01) | |
| *A61M 5/24* | (2006.01) | |
| *A61M 5/32* | (2006.01) | |
| *A61M 5/31* | (2006.01) | |
| *G01D 5/244* | (2006.01) | |
| *G01D 5/347* | (2006.01) | |
| *A61B 34/20* | (2016.01) | |

(52) U.S. Cl.
CPC ...... *A61M 5/3157* (2013.01); *A61M 5/31535* (2013.01); *A61M 5/347* (2013.01); *A61B 2034/2059* (2016.02); *A61M 2005/3126* (2013.01); *A61M 2005/3254* (2013.01); *A61M 2205/35* (2013.01); *A61M 2205/3569* (2013.01); *A61M 2205/50* (2013.01); *A61M 2205/505* (2013.01); *G01D 5/24461* (2013.01); *G01D 5/24471* (2013.01); *G01D 5/24476* (2013.01); *G01D 5/3473* (2013.01)

(58) Field of Classification Search
CPC ............. A61M 5/31568; A61M 5/168; A61M 5/16831; A61M 5/172; A61B 5/14532; A61B 5/4839; A61B 5/0002; A61B 5/4836; A61B 2034/2059; G16H 20/10; G16H 20/13; G16H 20/17; G01D 5/2454; G01D 5/2448; G01D 5/244; G01D 5/24457; G01D 5/24471; G01D 5/24461; G01D 5/24476; G01D 5/3473; G01D 5/2497
See application file for complete search history.

(56) References Cited

U.S. PATENT DOCUMENTS

| | | |
|---|---|---|
| 4,950,216 A | 8/1990 | Weder |
| 4,973,318 A | 11/1990 | Holm et al. |
| 4,988,660 A | 1/1991 | Campbell |
| 5,279,586 A | 1/1994 | Balkwill |
| 5,626,566 A | 5/1997 | Petersen et al. |
| 5,681,285 A | 10/1997 | Ford et al. |
| 5,822,715 A | 10/1998 | Worthington et al. |
| 5,925,021 A | 7/1999 | Castellano et al. |
| 5,933,106 A * | 8/1999 | He .................. H03M 5/22 341/116 |
| 5,984,900 A | 11/1999 | Mikkelsen |
| 6,004,297 A | 12/1999 | Steenfeldt-Jensen et al. |
| 6,042,571 A | 3/2000 | Hjertman et al. |
| 6,235,004 B1 | 5/2001 | Steenfeldt-Jensen et al. |
| 6,302,855 B1 | 10/2001 | Lav et al. |
| 6,482,185 B1 | 11/2002 | Hartmann |
| 6,817,986 B2 | 11/2004 | Slate et al. |
| 7,591,801 B2 | 9/2009 | Brauker et al. |
| 7,740,612 B2 | 6/2010 | Hochman |
| 7,905,833 B2 | 3/2011 | Brister et al. |
| 7,955,303 B2 | 6/2011 | Burren et al. |
| 7,976,492 B2 | 7/2011 | Brauker et al. |
| 8,221,356 B2 | 7/2012 | Enggaard et al. |
| 8,229,535 B2 | 7/2012 | Mensinger et al. |
| 8,231,531 B2 | 7/2012 | Brister et al. |
| RE43,834 E | 11/2012 | Steenfeldt-Jensen et al. |
| 8,460,231 B2 | 6/2013 | Brauker et al. |
| 8,565,848 B2 | 10/2013 | Brister et al. |
| D694,252 S | 11/2013 | Helm |
| 8,591,455 B2 | 11/2013 | Mensinger et al. |
| 8,663,109 B2 | 3/2014 | Brister et al. |
| 8,721,585 B2 | 5/2014 | Mensinger et al. |
| 8,750,955 B2 | 6/2014 | Mensinger et al. |
| 8,808,228 B2 | 8/2014 | Brister et al. |
| 8,882,741 B2 | 11/2014 | Brauker et al. |
| 8,920,401 B2 | 12/2014 | Brauker et al. |
| 8,926,585 B2 | 1/2015 | Brauker et al. |
| D727,928 S | 4/2015 | Allison et al. |
| 9,020,572 B2 | 4/2015 | Mensinger et al. |
| 9,050,413 B2 | 6/2015 | Brauker et al. |
| D738,385 S | 9/2015 | Lim et al. |
| 9,143,569 B2 | 9/2015 | Mensinger et al. |
| 9,155,843 B2 | 10/2015 | Brauker et al. |
| D747,333 S | 1/2016 | Supino et al. |
| D748,101 S | 1/2016 | Bang et al. |
| D748,126 S | 1/2016 | Sarukkai et al. |
| D749,103 S | 2/2016 | Song |
| D753,685 S | 4/2016 | Zimmerman et al. |
| D754,689 S | 4/2016 | Lee |
| D759,684 S | 6/2016 | Bijlani et al. |
| D761,280 S | 7/2016 | Chung et al. |
| D763,308 S | 8/2016 | Wang et al. |
| D766,958 S | 9/2016 | Salazar Cardozo et al. |
| 9,446,194 B2 | 9/2016 | Kamath et al. |
| D777,760 S | 1/2017 | Zhao et al. |
| D781,890 S | 3/2017 | Gathman et al. |
| D783,037 S | 4/2017 | Hariharan et al. |
| D783,648 S | 4/2017 | Vazquez et al. |
| D784,391 S | 4/2017 | Yuguchi et al. |
| D785,025 S | 4/2017 | Zimmerman et al. |
| D786,273 S | 5/2017 | Herman et al. |
| 9,672,328 B2 | 6/2017 | Saint |
| D791,806 S | 7/2017 | Brewington et al. |
| D794,047 S | 8/2017 | Gandhi et al. |
| D795,900 S | 8/2017 | Bischoff et al. |
| D795,919 S | 8/2017 | Bischoff et al. |
| D795,927 S | 8/2017 | Bischoff et al. |
| D797,760 S | 9/2017 | Tsujimura et al. |
| D798,312 S | 9/2017 | Tsujimura et al. |
| 9,775,543 B2 | 10/2017 | Brister et al. |
| D808,986 S | 1/2018 | Dudey |
| D809,544 S | 2/2018 | Ambielli |
| D809,545 S | 2/2018 | Ban et al. |
| D811,425 S | 2/2018 | Olsen et al. |
| D815,127 S | 4/2018 | Phillips et al. |
| D815,667 S | 4/2018 | Yeung |
| 9,937,293 B2 | 4/2018 | Brauker et al. |
| D819,043 S | 5/2018 | Yamaura et al. |
| D820,297 S | 6/2018 | Gardner et al. |
| 9,996,668 B2 | 6/2018 | Reihman et al. |
| D831,049 S | 10/2018 | Agarwal et al. |
| D831,684 S | 10/2018 | Ghosh |
| D832,292 S | 10/2018 | Hu et al. |
| D832,870 S | 11/2018 | Hu |
| D833,469 S | 11/2018 | Coleman et al. |
| D835,118 S | 12/2018 | Lee et al. |
| D837,807 S | 1/2019 | Baber et al. |
| D838,734 S | 1/2019 | Kruse et al. |
| 10,169,539 B2 | 1/2019 | Reihman et al. |
| D842,888 S | 3/2019 | Krainer et al. |
| D843,402 S | 3/2019 | Casse et al. |
| D846,590 S | 4/2019 | Cabrera et al. |
| D847,165 S | 4/2019 | Cheney et al. |
| D849,757 S | 5/2019 | Jing et al. |
| 10,278,580 B2 | 5/2019 | Brister et al. |
| 10,898,653 B2 * | 1/2021 | Saint .................. G08B 21/02 |
| 2003/0065536 A1 | 4/2003 | Hansen et al. |
| 2004/0039255 A1 | 2/2004 | Simonsen et al. |
| 2005/0038674 A1 | 2/2005 | Braig et al. |
| 2005/0049179 A1 | 3/2005 | Davidson et al. |
| 2005/0182358 A1 | 8/2005 | Veit et al. |
| 2005/0192494 A1 | 9/2005 | Ginsberg |
| 2005/0192557 A1 | 9/2005 | Brauker et al. |
| 2006/0036144 A1 | 2/2006 | Brister et al. |
| 2006/0052973 A1 * | 3/2006 | Hiller .................. G01D 5/24409 702/150 |
| 2006/0173417 A1 | 8/2006 | Rosen et al. |
| 2007/0021715 A1 | 1/2007 | Kohlbrenner et al. |
| 2007/0038044 A1 | 2/2007 | Dobbies et al. |
| 2007/0173708 A9 | 7/2007 | Dobbies et al. |
| 2007/0186923 A1 | 8/2007 | Poutiatine et al. |
| 2007/0239486 A1 | 10/2007 | Gordon |
| 2008/0162192 A1 | 7/2008 | Vonk et al. |
| 2008/0188813 A1 | 8/2008 | Miller et al. |
| 2008/0201169 A1 | 8/2008 | Galasso et al. |
| 2008/0234663 A1 | 9/2008 | Yodfat et al. |
| 2008/0235053 A1 | 9/2008 | Ray et al. |

(56) References Cited

U.S. PATENT DOCUMENTS

| | | |
|---|---|---|
| 2008/0262469 A1 | 10/2008 | Brister et al. |
| 2009/0036771 A1 | 2/2009 | Fago et al. |
| 2009/0048561 A1 | 2/2009 | Burren et al. |
| 2009/0069742 A1 | 3/2009 | Larsen |
| 2009/0131875 A1 | 5/2009 | Green |
| 2009/0163793 A1 | 6/2009 | Koehler |
| 2009/0209938 A1 | 8/2009 | Aalto-Setala |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0299276 A1 | 12/2009 | Brauker et al. |
| 2010/0049126 A1 | 2/2010 | Bronfeld et al. |
| 2010/0063438 A1 | 3/2010 | Bengtsson |
| 2010/0081993 A1 | 4/2010 | O'Connor |
| 2010/0185075 A1 | 7/2010 | Brister et al. |
| 2010/0261987 A1 | 10/2010 | Kamath et al. |
| 2010/0280329 A1* | 11/2010 | Randlov ............ A61B 5/14532 600/300 |
| 2010/0331656 A1 | 12/2010 | Mensinger et al. |
| 2010/0331657 A1 | 12/2010 | Mensinger et al. |
| 2011/0009727 A1 | 1/2011 | Mensinger et al. |
| 2011/0264033 A1 | 10/2011 | Jensen et al. |
| 2011/0270158 A1 | 11/2011 | Brauker et al. |
| 2011/0275986 A1 | 11/2011 | Bashan |
| 2011/0281791 A1 | 11/2011 | Zion et al. |
| 2011/0313349 A1 | 12/2011 | Krulevitch et al. |
| 2011/0313350 A1 | 12/2011 | Krulevitch et al. |
| 2011/0313395 A1 | 12/2011 | Krulevitch et al. |
| 2012/0072236 A1 | 3/2012 | Atkin |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0238852 A1 | 9/2012 | Brauker et al. |
| 2012/0296311 A1 | 11/2012 | Brauker et al. |
| 2013/0035575 A1 | 2/2013 | Mayou et al. |
| 2013/0035865 A1 | 2/2013 | Mayou et al. |
| 2013/0035871 A1 | 2/2013 | Mayou et al. |
| 2013/0171938 A1 | 7/2013 | Mears et al. |
| 2013/0184996 A1 | 7/2013 | Zivitz et al. |
| 2013/0197445 A1 | 8/2013 | Schabbach et al. |
| 2013/0197479 A1 | 8/2013 | Butler et al. |
| 2013/0211248 A1 | 8/2013 | Cowan et al. |
| 2013/0291116 A1 | 10/2013 | Homer |
| 2014/0012117 A1 | 1/2014 | Mensinger et al. |
| 2014/0012118 A1 | 1/2014 | Mensinger et al. |
| 2014/0012510 A1 | 1/2014 | Mensinger et al. |
| 2014/0012511 A1 | 1/2014 | Mensinger et al. |
| 2014/0074041 A1 | 3/2014 | Pedersen et al. |
| 2014/0113856 A1 | 4/2014 | Pohl et al. |
| 2014/0114158 A1 | 4/2014 | Brister et al. |
| 2014/0114161 A1 | 4/2014 | Kamath et al. |
| 2014/0257065 A1 | 9/2014 | Walsh |
| 2014/0276531 A1 | 9/2014 | Walsh |
| 2014/0288494 A1 | 9/2014 | Brister et al. |
| 2015/0073337 A1 | 3/2015 | Saint et al. |
| 2015/0202377 A1 | 7/2015 | Haupt |
| 2015/0351683 A1 | 12/2015 | Brauker et al. |
| 2015/0359965 A1 | 12/2015 | O'Connor et al. |
| 2016/0012205 A1* | 1/2016 | Saint ............. G16H 20/17 604/154 |
| 2016/0030683 A1 | 2/2016 | Taylor |
| 2016/0063734 A1* | 3/2016 | Divakaran ........... G06K 9/6202 382/110 |
| 2016/0066843 A1 | 3/2016 | Mensinger et al. |
| 2016/0081632 A1 | 3/2016 | Kamath et al. |
| 2016/0101232 A1 | 4/2016 | Kamath et al. |
| 2017/0068799 A1 | 3/2017 | Mensinger et al. |
| 2017/0124272 A1 | 5/2017 | Reihman et al. |
| 2017/0124275 A1 | 5/2017 | Reihman et al. |
| 2017/0124350 A1 | 5/2017 | Reihman et al. |
| 2017/0131993 A1 | 5/2017 | Salameh et al. |
| 2017/0132120 A1 | 5/2017 | Salameh et al. |
| 2017/0185283 A1 | 6/2017 | Bhavaraju et al. |
| 2017/0185284 A1 | 6/2017 | Bhavaraju et al. |
| 2017/0189625 A1 | 7/2017 | Cirillo et al. |
| 2017/0216518 A1* | 8/2017 | Davis ................. A61B 5/0015 |
| 2017/0270276 A1 | 9/2017 | Saint et al. |
| 2017/0286194 A1 | 10/2017 | Morris et al. |
| 2017/0286614 A1 | 10/2017 | Morris et al. |
| 2017/0366617 A1 | 12/2017 | Mensinger et al. |
| 2017/0367627 A1 | 12/2017 | Brister et al. |
| 2018/0185587 A1 | 7/2018 | Brauker et al. |
| 2018/0303417 A1 | 10/2018 | Mensinger et al. |
| 2018/0353698 A1 | 12/2018 | Saint et al. |
| 2019/0015020 A1 | 1/2019 | Brister et al. |
| 2019/0015596 A1 | 1/2019 | Saint et al. |
| 2019/0035500 A1 | 1/2019 | Saint et al. |
| 2019/0132801 A1 | 5/2019 | Kamath et al. |
| 2019/0173885 A1 | 6/2019 | Kamath et al. |
| 2019/0125224 A1 | 8/2019 | Kamath et al. |

FOREIGN PATENT DOCUMENTS

| | | | |
|---|---|---|---|
| EP | 513128 | 11/1992 | |
| EP | 927057 | 7/1999 | |
| EP | 1571582 A2 | 9/2005 | |
| EP | 2572740 | 3/2013 | |
| WO | 9638190 | 12/1996 | |
| WO | WO-2007069118 A2 * | 6/2007 | ......... G06F 19/3475 |
| WO | WO-2007069118 A3 | 9/2007 | |
| WO | 2010052275 | 5/2010 | |
| WO | 2011041007 | 4/2011 | |
| WO | 2012046199 | 4/2012 | |
| WO | 2013053695 | 4/2013 | |
| WO | 2014128157 | 8/2014 | |
| WO | 2015047870 | 4/2015 | |
| WO | 2015169814 | 11/2015 | |
| WO | 2015185686 | 12/2015 | |
| WO | 2016019192 A1 | 2/2016 | |
| WO | 2016071912 A1 | 5/2016 | |
| WO | 2017132577 A1 | 3/2018 | |

OTHER PUBLICATIONS

Copenheaver, B. R., Authorized Officer, ISA/US, International Search Report and Written Opinion, International Application No. PCT/US2014/056336, dated Dec. 31, 2014, 10 pages.

Young, Lee W., ISA/US, International Search Report, International Application No. PCT/US15/40069, dated Dec. 22, 2015, 13 pages.

Young, Lee W., ISA/US, Invitation to Pay Additional Fees and Partial Search Report, International Application No. PCT/US15/40069, dated Oct. 1, 2015, 2 pages.

Extended European Search Report for European Patent Application No. 14849422.2, dated May 4, 2017, 11 pages.

International Search Report and Written Opinion for PCT Application No. PCT/US2018/55646, dated Feb. 6, 2019, 15 pages.

International Search Report and Written Opinion for PCT Application No. PCT/US2017/15452, dated May 23, 2017, 14 pages.

Extended European Search Report for European Patent Application No. 17745019.4, dated Aug. 6, 2019, 9 pages.

International Search Report and Written Opinion for PCT Application No. PCT/US2018/036768; dated Aug. 31, 2018, 10 pages.

Curtiss B. Cook, et al: "The Intelligent Dosing System: Application for Insulin Therapy and Diabetes Management", Diabetis Technology & Therapeutics, vol. 7, No. 1, Feb. 1, 2005, pp. 58-71.

Extended European Search Report issued in corresponding application EP 18 81 4461.2 dated Feb. 19, 2021 (9 pages).

* cited by examiner

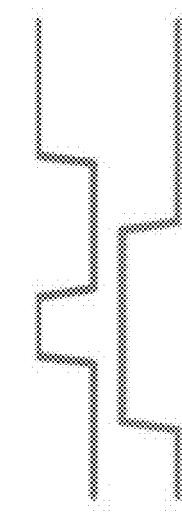
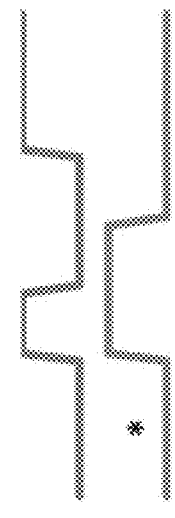
FIG. 8A
FIG. 8B
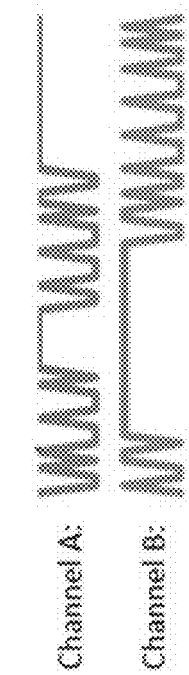
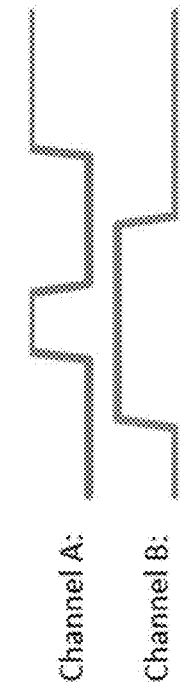
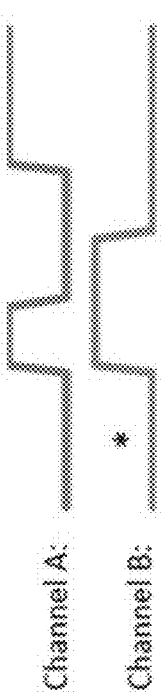
FIG. 8C
5 Edges
1 Out-of-order = 5 steps forward = 5 steps forward = 1 unit dose

INTELLIGENT MEDICATION DELIVERY SYSTEMS AND METHODS

CROSS-REFERENCE TO RELATED APPLICATIONS

This patent document claims priorities to and benefits of U.S. Provisional Patent Application No. 62/517,819 entitled "INTELLIGENT MEDICATION DELIVERY SYSTEMS AND METHODS" filed on Jun. 9, 2017. The entire content of the aforementioned patent application is incorporated by reference as part of the disclosure of this patent document.

TECHNICAL FIELD

This patent document relates to medicine administering and tracking systems, devices, and processes.

BACKGROUND

Diabetes mellitus, also referred to as diabetes, is a metabolic disease associated with high blood sugar due to insufficient production or use of insulin by the body. Diabetes is widely-spread globally, affecting hundreds of millions of people, and is among the leading causes of death globally. Diabetes has been categorized into three categories or types: type 1, type 2, and gestational diabetes. Type 1 diabetes is associated with the body's failure to produce sufficient levels of insulin for cells to uptake glucose. Type 2 diabetes is associated with insulin resistance, in which cells fail to use insulin properly. The third type of diabetes is commonly referred to as gestational diabetes, which can occur during pregnancy when a pregnant woman develops a high blood glucose level. Gestational diabetes can develop into type 2 diabetes, but often resolves after the pregnancy.

SUMMARY

Systems, devices, and techniques are disclosed for administering and tracking medicine to patients and providing health management capabilities for patients and caregivers.

In some aspects, a system for administering a medicine to a patient includes an injection pen device including a dose setting mechanism to set a dose of a medicine contained in a medicine cartridge that is to be dispensed by the injection pen device, a dispensing mechanism to dispense the medicine according to the set dose, and electronic circuits including a processor, a memory comprising instructions executable by the processor, and a wireless transmitter, the processor of the injection pen device configured to generate dose data associated with a dispensing event of a dose of the medicine dispensed from the injection pen device and time data associated with the dispensing event, and to wirelessly transmit the dose data; and a mobile communication device in wireless communication with the injection pen device, the mobile communication device including a data processing unit including a processor and memory to receive and process the dose data, wherein the mobile communication device includes a software application program product comprising a non-transitory computer-readable storage medium having instructions, which when executed by the processor of the data processing unit, cause the mobile communication device to determine a recommended dose based on health data and contextual data associated with a user of the injection pen device, the contextual data including one or more of physical activity data, location data, and nutrient data corresponding to a food, wherein the software application program product includes a data aggregator that obtains the health data and the contextual data, and a learning dose calculator that calculates the recommended dose of the medicine, wherein dose calculations by the learning dose calculator are adapted in accordance with data associated with time, location, activity, and food at a particular time and specific to the user of the injection pen device.

In some aspects, a method for determining a recommended dose of a medicine based on health data and contextual data associated with a user of a medicine injection pen device, the method comprising: receiving, at a computing device, one or more analyte values associated with a health condition of a user of the medicine injection pen device to which the medicine is associated; receiving, at the computing device, the health data and the contextual data associated with the user; determining, at the computing device, a set of dose calculator parameter settings specific to the user's current health state; calculating, at the computing device, a medicine dose value using the selected parameter settings; and generating, at the computing device, at least one of a displayable output or actuatable output based on the calculated medicine dose value, wherein the health data includes information pertaining to one or more of a previous dose of the medicine or a measured analyte of the user of the medicine injection pen device, and wherein the contextual data includes one or more of physical activity data, location data, and nutrient data corresponding to a food.

In some aspects, a method for processing signals from a mechanical encoder of a medicine injection pen device, the method comprising: receiving analog output signals from the mechanical encoder, the mechanical encoder comprising at least two signal channels; applying an asymmetric digital filter to the received analog output signals to produce a set of filtered signals; and applying a force pattern sequence to the filtered signals to resolve an out-of-order edge on one of the at least two channels to produce a set of noise-filtered and error-corrected encoder signals, wherein the produced noise-filtered and error-corrected encoder signals are associated with a dose setting of the medicine injection pen device.

In some aspects, a system for administering a medicine to a patient includes an injection pen device including a dose setting mechanism to set a dose of a medicine contained in a medicine cartridge that is to be dispensed by the injection pen device, a dispensing mechanism to dispense the medicine according to the set dose, a mechanical encoder comprising at least two channels operable to produce analog output signals corresponding to a dose setting, and electronic circuits including a processor, a memory, and a wireless transmitter, the processor of the pen device configured to generate dose data associated with a dispensing event of a dose of the medicine dispensed from the injection pen device and time data associated with the dispensing event, and to wirelessly transmit the dose data; and a mobile communication device in wireless communication with the injection pen device, the mobile communication device including a data processing unit including a processor and memory to receive and process the dose data, wherein at least one of the injection pen device or the mobile communication device includes a software application program product comprising a non-transitory computer-readable storage medium having instructions, which when executed by the processor, cause the at least one of the injection pen device or the mobile communication device to process signals from the mechanical encoder by: applying an asymmetric digital filter to the analog output signals to produce a set of filtered signals, and applying a force pattern sequence to the filtered signals to resolve an out-of-order edge on one of the at least two channels to produce a set of noise-filtered and error-corrected encoder signals.

BRIEF DESCRIPTION OF THE DRAWINGS

FIGS. 8A-8D show plots depicting example implementations of the noise filtering and error correcting method of FIG. 7.

DETAILED DESCRIPTION

Figure 1A:
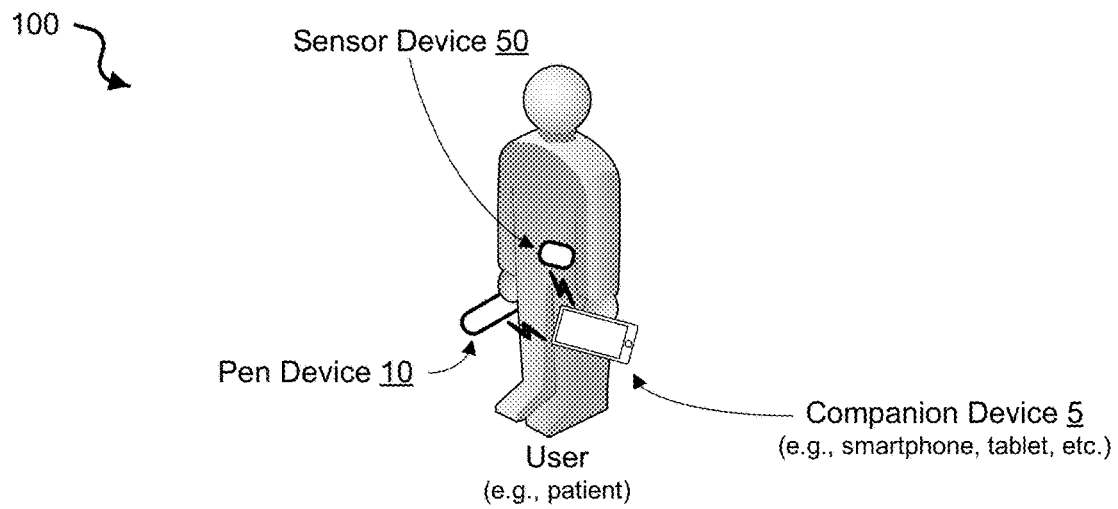
FIG. 1A shows a diagram of an example embodiment of an intelligent medicine administration system in accordance with the present technology.

Various diseases and medical conditions, such as diabetes, require a patient to self-administer doses of a fluid medication. Typically, when administering a fluid medication, the appropriate dose amount is set and dispensed by the patient using a syringe, a pen, or a pump. For example, self-administered medicaments or medicine include insulin used to treat diabetes, Follistim® used to treat infertility, or other injectable medicines such as Humira®, Enbrel®, Lovenox® and Ovidrel®, or others.

A medicament pen is a device that can be used to inject a quantity of a medicine (e.g., single or multiple boluses or doses of the medicine) into a user's body, where more than one dose can be stored in a medicine cartridge contained in the pen device. Pens offer the benefit of simplicity over other methods of delivery, such as syringe or pump-based methods. For example, syringes typically require more steps to deliver a dose, and pumps typically are more complicated to use and require a constant tether to the patient. However, previously there has not been an automated way to track and communicate the doses given with the pen in a simple, effective and reliable manner. In addition, it can be difficult to know how much to dose with the pen, when to dose, or if the patient dosed at all.

As with the dosing of any medication, it is sometimes hard for a patient to remember if a dose has been given. For this reason, for example, pill reminders have been developed where the patient places the medication for the day in a cup labeled with that day. Once they take their medication, there is no question it has been taken because the pills are no longer in the cup. Yet, there are no widely acceptable solutions that address this problem for injection-based therapies. Therefore, without simple, effective and reliable ways of tracking medicine doses, particularly for managing lifelong or chronic conditions like diabetes, patients may easily miss a dose or administer an incorrect dose (e.g., under-dose or over-dose) of their medicine which may result in serious, dangerous consequences to their health.

In addition to the challenges of tracking doses, calculating the right dose at the right time or under the right conditions is a widespread problem for patients of chronic conditions requiring daily dosing of medicine. Conventional dose calculators for administering insulin for Type I and Type II diabetes typically require manual estimation of carbohydrates ("carbs") at mealtime. For some users, carb counting and estimating may be too difficult, and some users may not utilize the dose calculator due to the manual work and number of steps required to do so, e.g., taking out one's smartphone, opening up an app, manually typing calculator inputs, etc.

Disclosed are intelligent medicine administration systems and methods that provide enhanced medicine dose recommendations for patient health management by the patient and their caregivers using medicine injection devices.

In some aspects, an intelligent medicine administration system includes a medicine injection device (also referred to as the "pen" or "pen device"), in communication with a patient's companion device (e.g., smartphone), in which the pen device is able to detect and record dose sizes dialed on the pen device and delivered, including the capability of distinguishing between a priming dose and a therapy dose. The companion device includes a software application ("app") having adaptive dose calculator and decision support modules to calculate and suggest the dose of a medicine (e.g., insulin) the patient should administer using the wirelessly connected medicine injection device, and to provide control over several functionalities of the medicine injection device, such as encoding and processing the signals associated with dose sizes for injection. For example, in some aspects, the system includes noise filtering and error correcting techniques for an encoder module, which can be implemented in the medicine injection device of the system.

Communication between the pen device and the companion device provides the ability for dose tracking, logging, calculating, recommending and/or communicating of dose data with a user (e.g., patient user, health care provider (HCP) and/or caregiver), and other advantages of the intelligent medicine administration system. For example, each bolus that is dispensed by the pen device can be automatically logged and communicated to the companion device.

FIG. 1A shows a diagram of an example embodiment of an intelligent medicine administering system 100 in accordance with the present technology. The system 100 includes a pen device 10 in wireless communication with a mobile computing and communication device 5 of a patient user, also referred to as the user's companion device. The pen device 10 is operable to select, set and/or dispense a dose of the medicine for dispensing. In some implementations, the companion device 5 includes a smartphone, tablet, and/or wearable computing device, such as a smartwatch, smartglasses, etc. In some implementations, the companion device 5 is in communication with other computing devices, such as a laptop and/or desktop computer, a smart television, or network-based server computer. The companion device 5 includes an app associated with the pen device 10 of the intelligent medicine administering system 100, which can monitor and/or control functionalities of the pen device 10 and to provide a dose calculator and/or decision support modules that can calculate and recommend a dose of the medicine for the patient user to administer using the pen device 10.

The companion device 5 can be used to obtain, process and/or display contextual data that can be used to relate to the patient user's health condition, including the condition for which the pen device 10 is used to treat. In an illustrative example, the companion device 5 is operable to track the patient user's location; the patient user's physical activity including step count, movement distance and/or intensity, estimated calories burned, and/or activity duration; and/or the patient user's interaction pattern with the companion device 5. The app associated with the system 100 can aggregate and process the contextual data to generate decision support outputs to guide and aid the patient user in using the pen device 10 and/or managing their behavior to promote better health outcomes in treating his/her health condition.

In some embodiments, the system 100 includes a sensor device 50 to monitor one or more health metrics of the patient user. Examples of health metric data monitored by the sensor device 50 include analytes, such as glucose, heart rate, blood pressure, user movement, or other. In some implementations, the sensor device 50 is a wearable sensor device such as a continuous glucose monitor (CGM) to obtain transcutaneous or blood glucose measurements that are processed to produce continuous glucose values. For example, the continuous glucose monitor can include a glucose processing module implemented on a stand-alone display device and/or implemented on the companion device 5, which processes, stores and displays the continuous glucose values for the patient user.

Figure 1B:
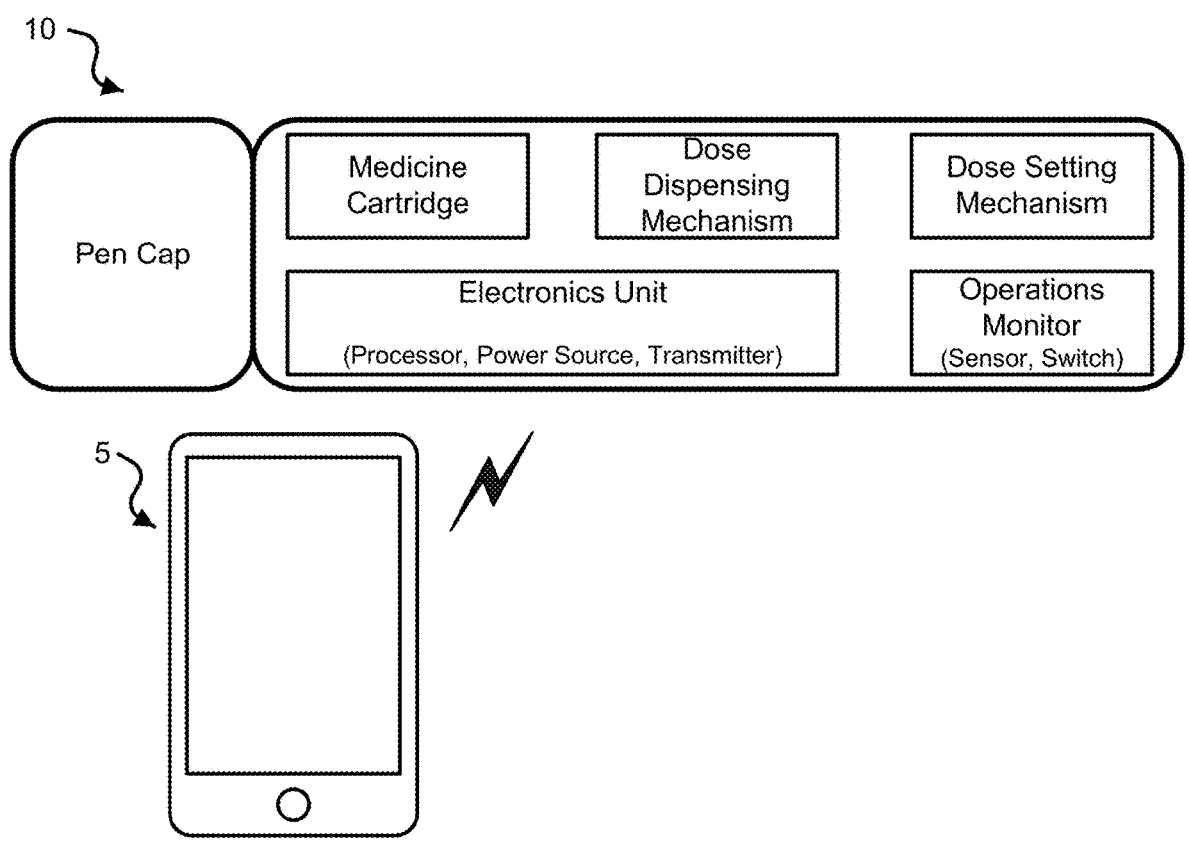
FIG. 1B shows a diagram of an example embodiment of a pen device in communication with a companion device of the intelligent medicine administration system of FIG. 1A.

FIG. 1B shows a diagram of an example embodiment of the pen device 10 of the intelligent medicine administering system 100. The pen 10 is structured to have a body which contains the medicine cartridge (e.g., which can be replaceable). The pen 10 is structured to include a dose dispensing mechanism to dispense (e.g., deliver) the medicine contained in the medicine cartridge out of the pen device 10; a dose setting mechanism to select and/or set the dose to be dispensed; an operations monitoring mechanism to determine that the pen device 10 is being operated and/or to monitor the operation of the dose being dispensed (e.g., such as a switch and/or sensor, or an encoder); and an electronics unit that can include a processor, a memory, a battery or other power source, and a transmitter.

The pen 10 is configured in communication with a user's mobile computing and communication device 5, e.g., such as the user's smartphone, tablet, and/or wearable computing device, such as a smartwatch, smartglasses, etc., and/or a user's laptop and/or desktop computer, a smart television, or network-based server computer.

In some implementations of the system 100, for example, to use the pen 10, the user first dials up a dose using a dose knob. The dose knob of the pen 10 can be included as part of the dose setting mechanism and/or the dose dispensing mechanism. For example, the dose may be adjusted up or down prior to administration of the dose. When the user applies a force against a dose dispensing button (e.g., presses against the dose dispensing button that is caused to protrude outward from the pen's body upon dialing the dose using the dose knob), a pushing component (e.g., also referred to as a 'plunger') of the dose dispensing mechanism is depressed against an abutment of the medicine cartridge loaded in the pen 10 to cause the pen 10 to begin to dispense the medicine, in which the quantity dispensed is in accordance with that set by the dose setting mechanism. In such implementations, the operations monitoring mechanism of the pen 10 will begin to sense movement of a rotating component or shaft that drives the plunger, for example, in which the movement is sensed through an encoder. In some examples, the encoder can be configured to sense the rotation of a component that is coupled to the drive shaft, and as the drive shaft rotates the plunger moves linearly; and therefore by sensing rotation of the component, the movement of the drive shaft and the plunger is sensed. Movement of the encoder may be detected as data processed by a processor of the electronics unit of the pen 10, which can be used to measure the dose. In some implementations, the processor can then store the size of the dose along with a time stamp for that dose. In some implementations, the pen 10 can then transmit the dose and related information to the companion device 5. In such implementations when the dose is transmitted, the data associated with the particular transmitted dose is marked in the memory of the pen 10 as transmitted. In such implementations if the dose was not yet transmitted to the companion device 5, then the data associated with the dose will be transmitted at the next time a successful communication link between the pen 10 and the companion device 5 is established.

The operations monitor mechanism of the pen 10 can include a sensor that can utilize any method of sensing rotary or linear movement. Non-limiting examples of such sensors include rotary and linear encoders, Hall effect and other magnetic based sensors, linearly variable displacement transducers, or any other appropriate method of sensing known in the art.

The dose dispensing mechanism of the pen 10 can include a manually powered mechanism or a motorized mechanism. In either case, a force (e.g., either produced by the patient or by an electrically-powered motor) pushes on the plunger of the dose dispensing mechanism to in turn force a receiving plunger of the medicament vial or cartridge to deliver the specific amount of the medicament. In some implementations, for example, the dose dispensing mechanism can be adjusted to deliver the dose over a different period of time. In one example, the dose dispensing mechanism can be operated such that the plunger is pushed in by an adjustable tension spring or change the speed of the motor to inject the dose over a time frame (e.g., 1 s, 5 s or other) to aid in reducing the pain of dosing. In one example, the dose dispensing mechanism can be operated over a much longer period of time, e.g., to better match the dynamics of carbohydrates, which can be like an extended bolus with a pump.

The software application (app) of the companion device 5, associated with the pen 10, provides a user interface to allow the user to manage his/her health related data. In some implementations, for example, the companion device 5 can be configured to control some functionalities of the pen device 10. In some implementations, for example, the companion device 5 includes the user's existing smartphone, tablet, or wearable computing device. In some implementations, for example, the companion device 5 is an independent portable device that the user may carry on his/her person. In one example embodiments of an independent portable companion device 5, the companion device 5 includes a data processing unit, wireless communication unit to allow the device to communicate with the pen device 10, and a display unit.

Figure 1C:
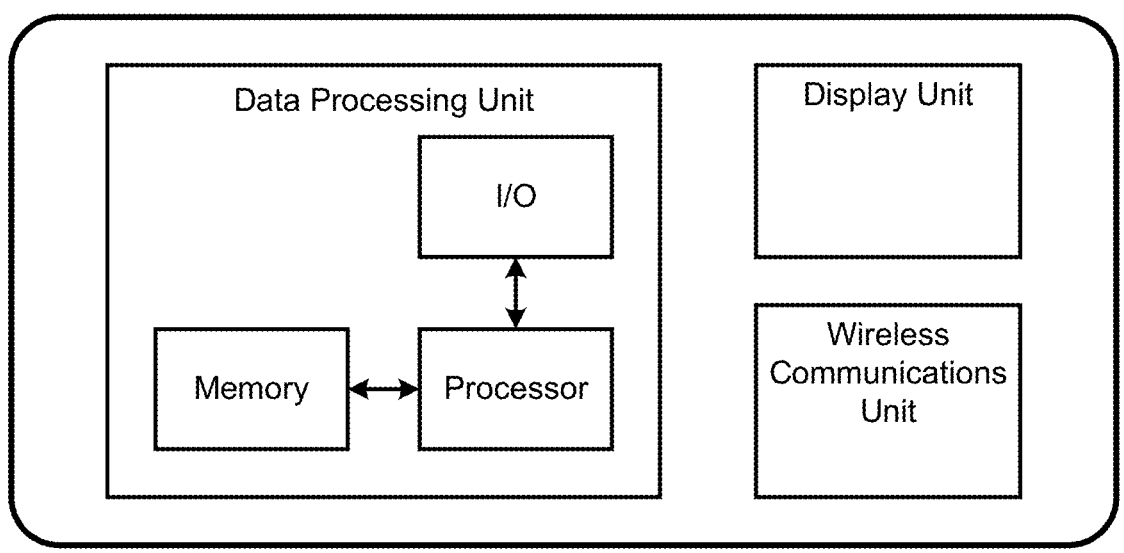
FIG. 1C shows a block diagram of an example embodiment of the companion device of the intelligent medicine administering system of FIG. 1A.

FIG. 1C shows a block diagram of an example embodiment of the companion device 5 of the intelligent medicine administration system 100. The data processing unit of the companion device 5 includes a processor to process data, a memory in communication with the processor to store data, and an input/output unit (I/O) to interface the processor and/or memory to other modules, units or devices of the companion device 5 or external devices. For example, the processor can include a central processing unit (CPU) or a microcontroller unit (MCU). For example, the memory can include and store processor-executable code, which when executed by the processor, configures the data processing unit to perform various operations, e.g., such as receiving information, commands, and/or data, processing information and data, and transmitting or providing information/data to another device. In some implementations, the data processing unit can transmit raw or processed data to a computer system or communication network accessible via the Internet (referred to as 'the cloud') that includes one or more remote computational processing devices (e.g., servers in the cloud). To support various functions of the data processing unit, the memory can store information and data, such as instructions, software, values, images, and other data processed or referenced by the processor. For example, various types of Random Access Memory (RAM) devices, Read Only Memory (ROM) devices, Flash Memory devices, and other suitable storage media can be used to implement storage functions of the memory unit. The I/O of the data processing unit can interface the data processing unit with the wireless communications unit to utilize various types of wired or wireless interfaces compatible with typical data communication standards, for example, which can be used in communications of the data processing unit with other devices such as the pen device 10, via a wireless transmitter/receiver (Tx/Rx) unit, e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, NFC (Near Field Communication), and parallel interfaces. The I/O of the data processing unit can also interface with other external interfaces, sources of data storage, and/or visual or audio display devices, etc. to retrieve and transfer data and information that can be processed by the processor, stored in the memory unit, or exhibited on an output unit of the companion device 5 or an external device. For example, a display unit of the companion device 5 can be configured to be in data communication with the data processing unit, e.g., via the I/O, to provide a visual display, an audio display, and/or other sensory display that produces the user interface of the software application of the disclosed technology for health management. In some examples, the display unit can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

In various operations of the disclosed intelligent medicine administration system, for example, when a dosing event (e.g., an amount of fluid is dispensed from the pen device 10), a time stamp associated with the dispensing is referenced is recorded by the processing unit of the pen 10 (e.g., stored in the memory of the pen 10). For example, the time stamp may be the current time or a time where a count-up timer is used. When the dose information is eventually transmitted to the companion device 5, the time stamp and/or a 'time-since-dose' parameter is transmitted by the pen 10 and received by the companion device 5 and stored in the memory of the data processing unit of the companion device 5. In some implementations, for example, the time of the dose can be determined without the pen having to know the current time. This can simplify operation and setup of the pen 10. In some implementations, for example, a user time is initialized on the pen 10 from the companion device 5, in which the user time is used for dose time tracking. Using the system 100, the companion device 5 can know the time of the dose relative to the current time.

Once the companion device 5 receives the dose related information (e.g., which can include the time information and dose setting and/or dispensing information, and other information about the pen 10 related to the dosing event), the companion device 5 stores the dose related information in memory, e.g., which can include among a list of doses or dosing events.

For example, via the software application's user interface, the companion device 5 allows the patient to browse a list of previous doses, to view an estimate of current medicament active in the patient's body ("medicament on board") based on calculations performed by a medicine calculation module of the software application, and/or to utilize a dose calculation module of the software application to assist the patient regarding dose setting information on the size of the next dose to be delivered. For example, the patient could enter carbohydrates to be eaten, current blood sugar, and the companion device 5 would already know insulin on board. Using these parameters a suggested medicine dose (e.g., such as insulin dose), calculated by the dose calculation module, may be determined. In some implementations, for example, the companion device 5 can also allow the patient to manually enter boluses into the pen device 10 or another medicine delivery device. This would be useful if the patient was forced to use a syringe, or if the battery in the pen device 10 was depleted.

Figure 1D:
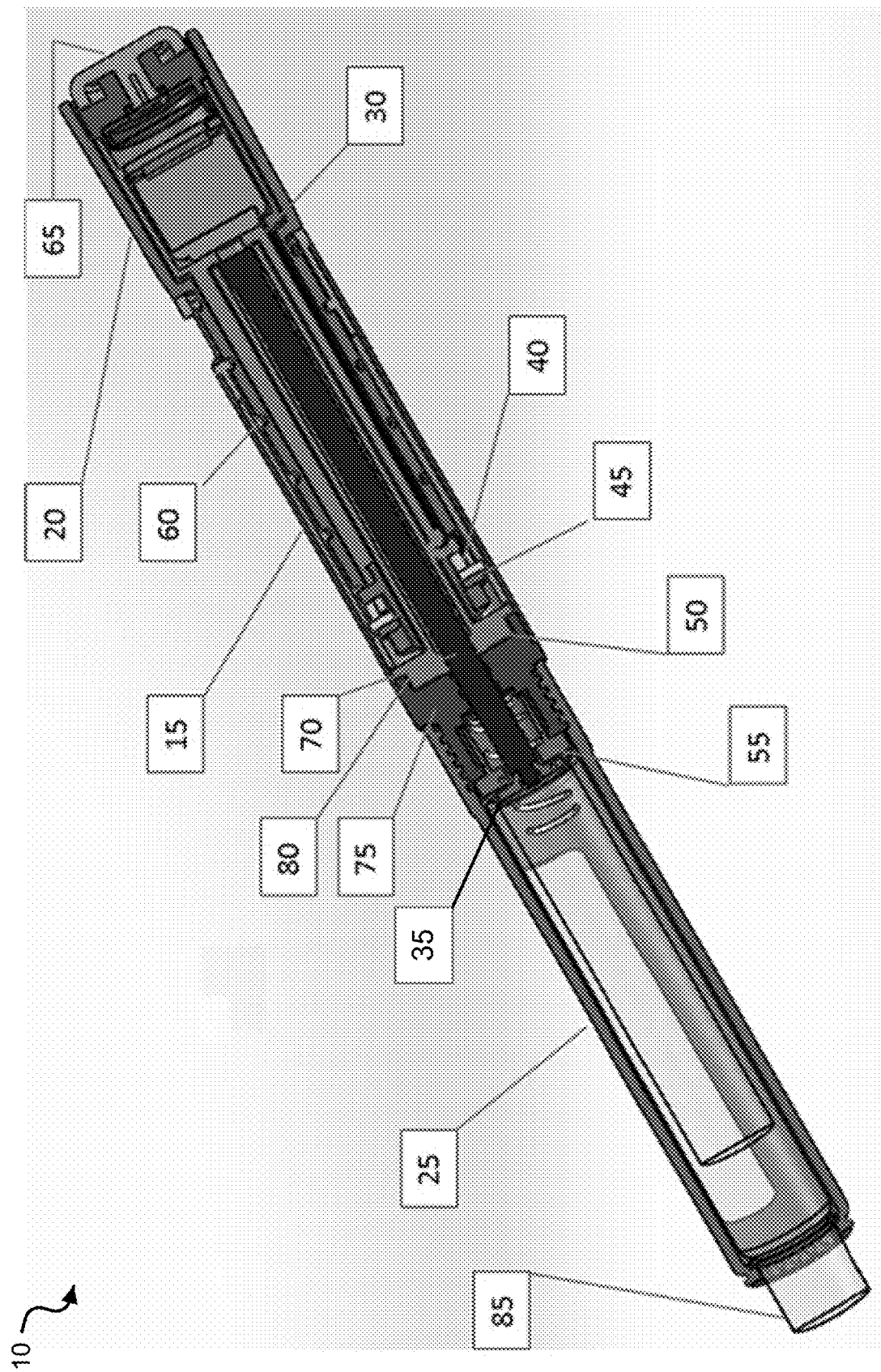
FIG. 1D shows a schematic illustration of an example embodiment of the pen device shown in FIG. 1B.

FIG. 1D shows a schematic illustration of an example embodiment of the pen device 10. The example shown in FIG. 1D illustrates the structural arrangement and interaction of the example modular units and mechanisms depicted in FIG. 1B for various operations of the pen device 10. As shown in FIG. 1D, the pen device 10 includes a mechanism to actuate a force to cause a displacement of a piston which resides within a medicament vial or cartridge 85. The displacement of the piston of the medicament vial 85 forces a volume of the medicament (that is proportional to the displacement of the piston) out of the vial 85, e.g., allowing it to be injected into a patient. The vial 85 is held within a medicament housing 25 of the pen device 10. The medicament housing 25 attaches to a main body housing 15 of the pen device 10, which includes a dose setting and dispensing mechanism and electronics unit of the pen device 10. In some embodiments, for example, the medicament housing 25 and the main body housing 15 may be a singular housing structure. The medicament housing 25 is structured to include a chamber to hold and/or encase the medicament vial 85 within the housing 25 of the pen device 10. The pen device 10 can also include a detachable pen cap (not shown) to cover an end of the pen device 10 that exposes a needle assembly (not shown) of the pen device 10 to disburse the medicine out of the pen device 10 when dispensed from the vial 85. The pen device 10 can include a vial spring 35, which provides a force on a screw retractor 55 to push the medicament vial 85 into the medicament housing 25 to ensure good dose accuracy. The pen device 10 includes a dose knob 20 attached to or included as part of the housing 15, where the dose knob is coupled to the housing by a non-self-locking thread 60. In some embodiments, for example, an electronics housing 30 may reside within the dose knob 20, in which the electronics housing 30 contains the electronics unit of the pen device 10. The dose setting mechanism includes a dose knob 20. When the dose knob 20 is rotated into or out of the housing 15 to adjust the dose, the electronics housing 30 does not turn. However, when translational or axial force is placed to the dose button 65 (e.g., in which resides the electronics housing), a catch structure component is engaged to lock the electronics housing 30 and dose knob 20 together, forcing them to rotate together as the pair travel back into the housing 15 upon actuation of the dose dispensing mechanism to apply force to the dose knob 20 to cause dispensing of the set dose. The rotation of the dose knob 20, e.g., which can be via the electronics housing 30, rotates a shaft 50 (e.g., which can be configured as a bi-directional clutch shaft). The shaft 50 in turn rotates a dose screw 70 which rides within a nut 75 which is fixed to the housing 15. This rotation causes the dose screw 70 to extend out of the housing 15 causing an injection of medicament. In some embodiments, for example, the dose dispensing mechanism can include a friction-causing structure 80, e.g., which can be coupled to the exemplary bi-directional clutch shaft 50 to present a frictionous surface (i.e., a surface that provides friction) to make contact with the nut 75 or housing body 15 or other internal structure of the dose dispensing mechanism, which acts from the bi-directional clutch shaft 50 to the housing 15 or nut 75 to prevent rotation of the shaft 50 while the dose setting mechanism is being adjusted via turning of the dose knob 20, but also allowing the friction to be overcome during the dose dispensing operation. In addition, by overcoming friction in the opposite direction the dose screw 70 may be driven back into the housing 15 and prepared for a new cartridge of medicament to be loaded. In some embodiments, for example, the pen device 10 includes a screw retractor component 55 that is axially fixed to the housing but rotationally free. The screw retractor component 55 is operable to be bent in to "grab" the non-circular cross section of the dose screw 70 allowing it to be rotated relative to the housing 15 and driven back into the housing 15. In some implementations, for example, the components of the pen device 10 could be manufactured by injection molding, machining or other similar process. In embodiments including the bi-directional clutch shaft, for example, the pen device 10 is capable of allowing retraction of the lead screw, and repeatability of operation of the dose dispensing mechanism.

In some embodiments, the sensor unit of the pen device 10 includes a rotational encoder, for example, between the dose knob 20 (e.g., which can be coupled to the jack screw) and the housing 15, and in electrical communication with the electronics unit contained in the electronics housing 30. The encoder is included in a sensor unit to determine the quantity of the dose set by the dose setting mechanism, and/or, the quantity of the dose dispensed by the dose dispensing mechanism. In some implementations, for example, the encoder can be configured in the pen device 10 to determine the dispensed dose by detecting rotation of the lead screw which is correlated with displacement of the pusher foot which is correlated with displacement of the receiving plunger in the vial 85, which in turn is correlated with dispensed insulin. In some embodiments, for example, the encoder can include two flat plates with contacts in between them. The plates are aligned perpendicular to the axis of the device. For one plate, a contact plate 40 is rotationally fixed to the jack screw, e.g., which can be via the electronics housing 30; and for the other plate, a code wheel 45 is rotationally fixed to the housing 15. In implementations, for example, when relative motion occurs between these two plates during dosing, the relative motion is measured and transmitted to the data processing and communications unit for processing, storage and/or transmission to the companion device 5.

In some embodiments of the pen device 10, for example, the dose setting and dispensing mechanism may include a mechanism in which the dose screw 70 is comprised of an elongate nut which screws in and out of the housing to provide dosing. The nut component in the previous described embodiment (e.g., nut 75) can include a separate screw structure; whereas in this embodiment of the dose screw, the nut component is part of the dose screw including exterior threads and is coupled to the housing 15. When the exemplary bi-directional clutch shaft 50 provides rotation, it operates on the jack screw, e.g., in which the dosing nut in this case threading it out of the housing.

Example embodiments and implementations of the disclosed intelligent medicine administration system are described. While the disclosed embodiments described herein are primarily based on diabetes management systems and methods involving insulin pen and glucose monitoring devices to facilitate understanding of the underlying concepts, it is understood that the disclosed embodiments can also include treatment of other health conditions using other medications by the pen device and/or monitoring of other analytes by sensor devices.

Adaptive Dose Calculator and Decision Support Modules

In some aspects, the intelligent medicament delivery system 100 includes an adaptive dose calculator and decision support modules to determine and recommend a time- and circumstance-relevant dose of a medicine (e.g., insulin) for the patient, and in some implementations provide control over the pen device 10 to set the dose. In some example implementations, dose data is determined and provided by the app on the companion device 5 to the pen device 10, e.g., to set a recommended insulin dose, and the intelligent medicament delivery system 100 is able to provide a time- and circumstance-relevant dose of insulin based on real-time knowledge of glucose levels, e.g., provided by the example glucose sensor device 50 such as a CGM or smart blood glucose meter (e.g., smart BGM), and knowledge of insulin on board (IOB), e.g., provided by the pen device 10. In some examples, IOB can additionally or alternatively be provided by an insulin pump being used by the patient user, e.g., as some diabetic patient users may choose to alternate insulin pump use with an insulin pen for a time being and/or use an insulin pen as a supplement medication delivery device to the insulin pump.

Figure 2:
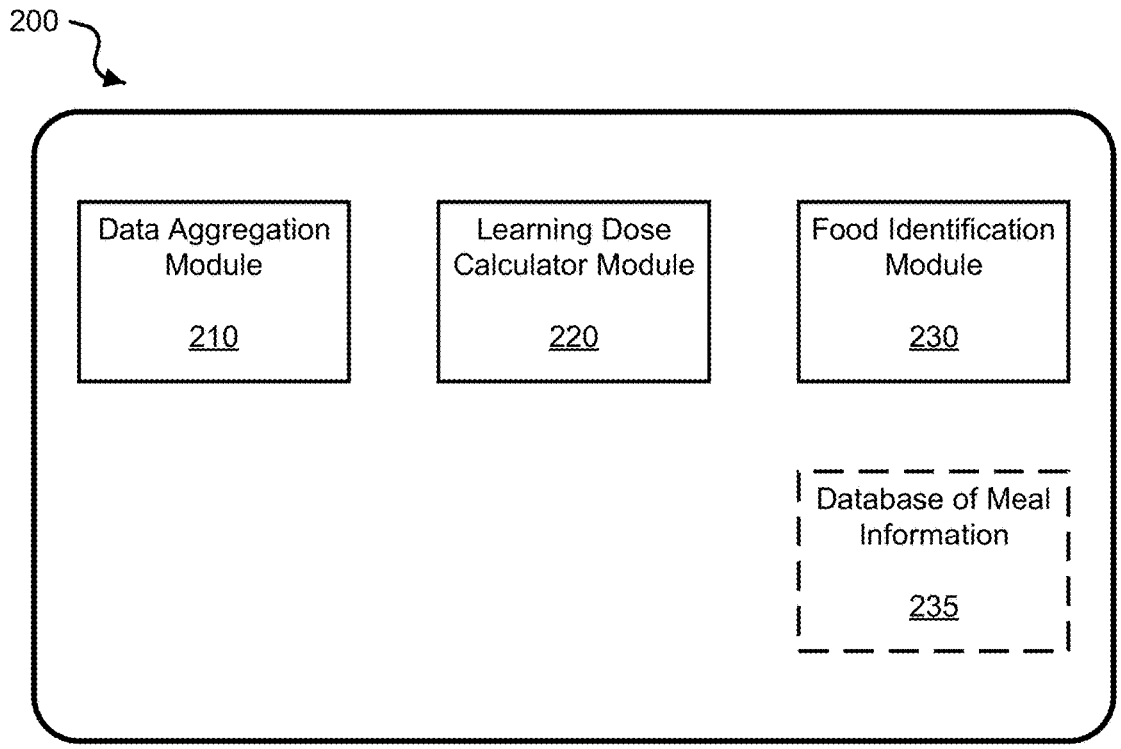
FIG. 2 shows a diagram of an example software architecture of data processing modules in accordance with some example embodiments of the intelligent medicine administration system.

FIG. 2 shows a diagram of an example software architecture of data processing modules in some example embodiments of the app of the intelligent medicine administrating system 100. The diagram depicts an example software architecture 200 for processing health data and contextual data obtained by the app on the companion device 5 from the pen device 10, from the sensor device 50, and/or from other devices of the patient user and/or apps on the companion device 5. In some embodiments, the software architecture 200 is embodied as part of the app resident on the companion device 5. Similarly, in some embodiments, for example, the software architecture 200 can be embodied as part of a data processing system in the cloud (e.g., resident on one or more cloud computers). In some embodiments, the software architecture 200 is embodied as part of both the software app on the companion device 5 and the data processing system in the cloud, in which some or all of the modules of the software architecture 200 are shared or divided among the app on the companion device 5 and the data processing system in the cloud.

As shown in FIG. 2, the software architecture 200 includes a data aggregator module 210 configured to obtain the health data from a device, such as the pen device 10, sensor device 50, and/or other devices or apps in communication with the companion device 5. The software architecture 200 includes a learning dose calculator module 220 to adaptively and autonomously calculate a dose of the medicine associated with dose injections from the pen device 10 based on time-relevant and context or circumstances-relevant data specific to the patient user of the pen device 10. The software architecture 200 includes a food identification module 230 to process data associated with food, activity, and other contextual data for use by the learning dose calculator module 220. In some implementations of the system 100, the learning dose calculator module 220 and/or the food identification module 230 receives data from the data aggregation module 210 to be processed by the respective modules 220 and/or 230. In some embodiments, the software architecture 200 may include or interface with a meal information database 235, which can be a database in the cloud, in communication with the software app on the companion device 5 to store information about meals to be accessible to the various modules of the software app. In some implementations, the food identification module 230 is configured to receive and store at least some meal information provided from the meal information database 235 (e.g., which may be via the data aggregation module 210).

The example modules shown in the software architecture diagram can be organized to provide data to one another in various ways, including directly (e.g., module-to-module) and/or indirectly (e.g., via an intermediary module), based on a periodic, an intermittent, and/or a per-request basis.

It is noted that while the app is described as resident on the companion device 5, it is understood that some or all of the software modules of the app may be resident on the pen device 10 or in a centralized networked computer server, e.g., the cloud, and may be distributed across multiple locations.

Learning Dose Calculator

In some example embodiments of the app resident on the companion device 5, the learning dose calculator module 220 is configured to receive and process health data and user contextual data to calculate a time-relevant and circumstance-relevant dose amount that the system recommends to the patient to dose. For example, the health data can include information pertaining to the medicine to dose (e.g., type of medicine in the pen device 10 to dose, such as type of insulin; previous amount or amounts dosed, such as last dose or a historical dose; and/or other medicines used by the patient), information pertaining to a measured analyte (e.g., glucose value, including present glucose values, present glucose trend, and/or historical glucose values and trends), and other health-related information including heart rate, blood pressure, menstrual cycle, etc. For example, contextual data can include food intake (e.g., amount of carbs and/or total calories), physical activity (e.g., timing of activity or exercise, associated calories burned, etc.), the patient's location (e.g., at a restaurant, gym, home, etc.), the patient's mental state, and other data related to the patient's behavior and lifestyle. The learning dose calculator module 220 can receive data from one or more devices of the patient user, such as the pen device 10, an analyte sensor device 50 such as a glucose meter (e.g., continuous glucose monitor (CGM) device or single measurement blood glucose meter (SMBG) device), and/or activity monitors (e.g., activity or exercise watch or smartwatch, pedometer, and the like). The learning dose calculator module 220 can receive data from other software applications resident on the companion device 5, e.g., such as health aggregation apps like Apple HealthKit and/or Google Fit, and the like.

Figure 3:
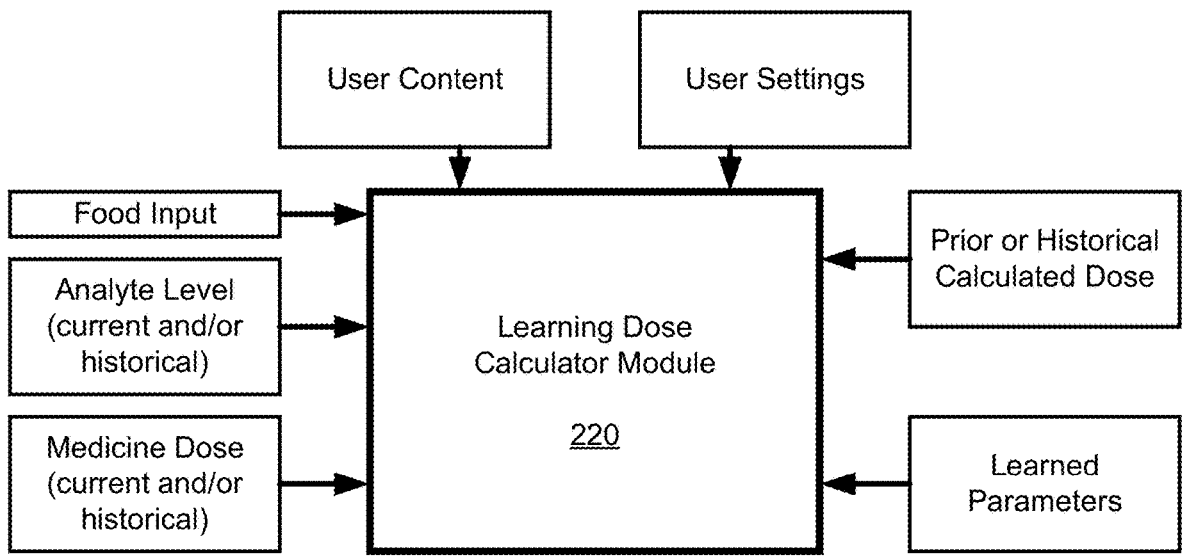
FIG. 3 shows a diagram illustrating an example implementation of health data and user contextual data processable at a learning dose calculator module in accordance with some example embodiments of the intelligent medicine administration system.

FIG. 3 shows a diagram illustrating an example implementation of health data and user contextual data received at the learning dose calculator module 220 for time-relevant and circumstance-relevant dose calculations for the system 100. For example, the learning dose calculator module 220 can process the inputted data to generate an output that is executable on the pen device 10 to affect dose administration (e.g., dose setting and/or display) and/or that is displayable to the patient on the companion device 5 and/or the pen device 10. As depicted in the example, aggregated data such as food input, analyte level(s) (e.g., current and/or historical), medicine dose(s) (e.g., current and/or historical), and user content information and system device data such as user device settings, previous and/or historic calculated doses by the learning dose calculator module 220, and/or learned parameters for the learning dose calculator module 220 and/or pen device 10 or app operation are submitted to the learning dose calculator module 220.

The learning dose calculator module 220 dynamically factors patient parameters that can be entered by a user (e.g., the patient user and/or an authorized user such as the patient's physician or caregiver) and/or parameters determined from data tracked by the app (e.g., from the pen device 10 and/or pulled from another app such as a health aggregation app). In some implementations, the learning dose calculator module 220 can determine a recommended dose of the medicine loaded in the pen device based on established clinical rules and/or aggregated data from larger populations (i.e. "crowdsourced" data), using patient-specific parameters such as weight, gender, ethnicity, and/or height (BMI), total daily dose, carb intake, physical activity, etc. For example, established clinical rules and norms for dose calculations are discussed in "Pumping Insulin" by John Walsh, Torrey Pines Press; 3 edition (January 2000), e.g., in Chapter 12 "Select, Test, and Adjust Your Carb Factor."

The learning dose calculator is configured to account for improved carb factors, correction factors and duration of insulin action based on certain established clinical rules. For example, in implementations, the learning dose calculator module 220 automatically updates and modifies variables such carb factors, correction factors, and duration of insulin action based on the certain rules of the dose calculator, in which the modified variables feed back into the dose calculator algorithm. The app can provide these modified parameters and the present and/or historical recommended/calculated dose values to the patient user's health care provider (HCP) or other caregiver, e.g., via the cloud. For example, in some implementations, the HCP or caregiver can be provided the modified variables for approval, e.g., prior to their incorporation to produce the recommended calculated dose.

The learning dose calculator may set carb factors and correction factors independently using non-confounded data, or together using a multivariable linear regression fit (e.g., calculating the response surface). In an example, if determining independently, the correction factor may preferably be set first (e.g., based on doses taken for blood glucose (BG) correction only and not for covering carbs), because BG data is based on a calibrated BG meter or sensor and is less prone to error than the user's estimation of carbs eaten. Once the correction factor is set, it may be accounted for in carb-covering doses to determine the correct carb factor. Alternatively, for example, a history of doses taken for carb covering and/or BG correction may be analyzed as a whole, calculating the response surface and explicitly determining the user's true carb factor and correction factor from past data.

Further, the amount of noise or scatter in the carb factor response surface (e.g., how closely the true data matches a linear fit) is an approximate measure of how accurately the user is estimating the carbs in their meals. The goal of setting the carb factor is not necessarily to set it to the most correct average value, as that may lead to unsafe doses when the user over-estimates carbs. Instead, it may be biased downward to ensure that even if the user over-estimates carbs (perhaps based on the $20^{th}$ percentile of high estimates) it will result in a nominal or at least safe final glucose value. Further, an unusually high amount of scatter in the data may prompt patient education or used as a metric reported to the physician indicating that the user may need help counting carbs or may consider a therapy method other than carb counting.

The learning dose calculator module 220 can include safe zones or percentages to allow the algorithm to work within, e.g., in which in some implementations these safe zones can be specified by the HCP or the patient user. In some implementations, the HCP can override the modified variables and turn off the "learning" feature of the learning dose calculator module 220 automatically.

The learning dose calculator module 220 is configured to compare metrics of exercise (e.g., steps), and if sufficient activity or exercise is detected, generate an output indicative of a warning to be provided to the patient user that their present dose setting (e.g., previous dose calculation) may suggest too many carbs due to their recent exercise. The learning dose calculator module 220 is configured to use hypoglycemia as a metric or gain to the learning algorithm, e.g., to make user specific. For example, the learning dose calculator module 220 can be configured to make variables more conservative until acceptable levels of hypoglycemia are reached.

In some implementations, such as for insulin dose calculation, for example, the learning dose calculator module 220 is configured to adjust the recommended dose based on the type of input data, such as the type of analyte measurements, e.g., glucose data from a CGM device versus from a non-continuous glucose meter such as a SMBG device ("fingerstick"). For example, since a typical CGM device provides alarms that act as a safeguard against hypoglycemia, the algorithm of the learning dose calculator can be configured to dose more conservatively if CGM data is not available. For example, since a typical CGM device provides glucose trend information, trend data can be accounted for by the learning dose calculator module 220 in calculations to calculate dose or predicted glucose, rather than just relying on an instantaneous glucose value. In some implementations, the learning dose calculator can calculate based on glucose trend and current glucose value that includes knowledge of carbs, insulin, exercise, etc., to produce a dose calculator based on a forecasted trend using such information. In some implementations, the learning dose calculator can adjust an insulin recommendation based on recent glucose trend. For example, if glucose is rising within a certain range, a set amount of additional insulin may be added to the recommendation.

In some implementations, the learning dose calculator module 220 is configured to base a dose calculation, at least in part, on the patient's reported A1C. For example, the learning dose calculator module 220 may adjust a target glucose value or 'aggressiveness' of the dosing schedule based on A1C in the app.

In some implementations, the learning dose calculator module 220 can calculate a current and forecasted "insulin deficit" value, meaning the additional amount of insulin needed to bring the user back to a target glucose level. For example, app can show, via a display screen of the companion device 5, a real-time display of the currently calculated glucose correction dose (e.g., insulin deficit) whenever the app has access to current glucose data, e.g., from a CGM device or connected BG meter. This could be shown by the app, e.g., or on a widget of the companion device 5 or a corresponding app on a peripheral device such as a smartwatch, and/or as a persistent notification on such devices. For example, the user may also view forecasted insulin deficit/recommended dose in the future based on trended or forecasted glucose values. In some implementations, an alarm is generated based on the output of the learning dose calculator module 220 when the calculated dose of at least a certain amount of medicine (e.g., user settable amount) is needed to get back to the target analyte (e.g., glucose) value.

In some implementations, the learning dose calculator module 220 can produce an output indicative of recommending exercise, e.g., in lieu of insulin to lower a glucose level. For example, known exercise routines such as a 5 minute walk or 15 minutes of cardio may be calibrated for that particular user, based on past experience of how much they lower glucose. The example algorithm can base the calculated exercise recommendation on one or more of several factors, including insulin on board (IOB), food recently eaten, time of day, other recent exercise, and other parameters used by a calculation algorithm. The learning dose calculator module 220 can track activity by monitoring accelerometer data, e.g., from the pen device itself, and/or from the companion device 5, and/or based on data from other wearable devices (such as activity monitors like a Fitbit, for example) to adjust dose calculations/recommendations.

Forecasted glucose values and/or recommended insulin may be modified based on known effects of exercise to lower glucose levels. Tracking exercise in real-time can passively inform the algorithm of the learning dose calculator module 220 about the effects exercise has on the particular patient's glucose level, to be used for future calculations.

In some implementations, for example, the learning dose calculator module 220 is configured to prompt the patient user to check after a dose based on a determined probability, e.g., by the dose calculator, that a glucose level will be out of range. Examples include after a particularly large dose, after a particularly high or low glucose level when dose was taken, and excessively high carb consumption.

In some implementations, for example, the learning dose calculator module 220 is configured to stagger partial-doses based on certain, patient specific circumstances. In an illustrative example, the learning dose calculator module 220 is configured stagger partial-doses based on foods with known slow glycemic response. For example, pizza may prompt for a partial correction dose immediately and the rest of the dose an hour later to try to maintain a flat glucose response. This partial correction may be based on the user's own history with this or similar foods, and/or aggregated data from a larger population of users who have all had experience with this type of food. The learning dose calculator module 220 can provide a dose reminder automatically set for (in this example) an hour later. In some implementations, for example, the learning dose calculator module 220 is configured to also adjust a second dose based on glucose level, or prompt for a glucose measurement before recommending the second dose.

For example, when a glucose level is low and the app recommends eating, in addition to simply listing number of grams of carbs to eat, the learning dose calculator module 220 of the app may convert that to some amount of a particular food. This could be user-defined or selected from a list of suggestions. For example, in addition to "Eat 15 grams of carbs" or the like, the app could display "one slice of bread." Similarly, a list of possible foods could be displayed, e.g., 1 slice bread, or 1 banana, or 1.7 chicken nuggets (e.g., with brand info). In some implementations, for example, the learning dose calculator module 220 is configured to base recommendations on location, with items from nearby restaurants or other common places the person eats. Food equivalents to carbs may also be randomly displayed on the app to help educate the user over time.

In some implementations, for example, the learning dose calculator module 220 is configured to automatically adjust dose calculator recommendations based on past success for a specific food. For example, if the typical dose recommended for pizza always leaves the patient with higher glucose than desired, the learning dose calculator module 220 can add an offset to future recommendations to better achieve target when calculations consider this type of food. Such offsets can be aggregated (e.g., "crowdsourced") across many users, helping identify foods that commonly need adjustment. This could be presented as an alert to the patient, or automatically integrated as an offset or scaling factor for the default dose recommendation for that food. In some implementations, the system can crowdsource nutritional content of meals. This could determine nutritional information for unlabeled foods and also foods that may be mislabeled. For example, in some implementations, the system can include a database of effective carb content of foods so that the system, via the app using the learning dose calculator module 220, can make better dose recommendations when those foods are eaten. The effective carb content may not reflect the food's actual carbohydrate content, but would be related only to the amount of insulin needed when the food is eaten, thereby compensating for other effects on metabolism or other nutrients in the food.

Figure 4A:
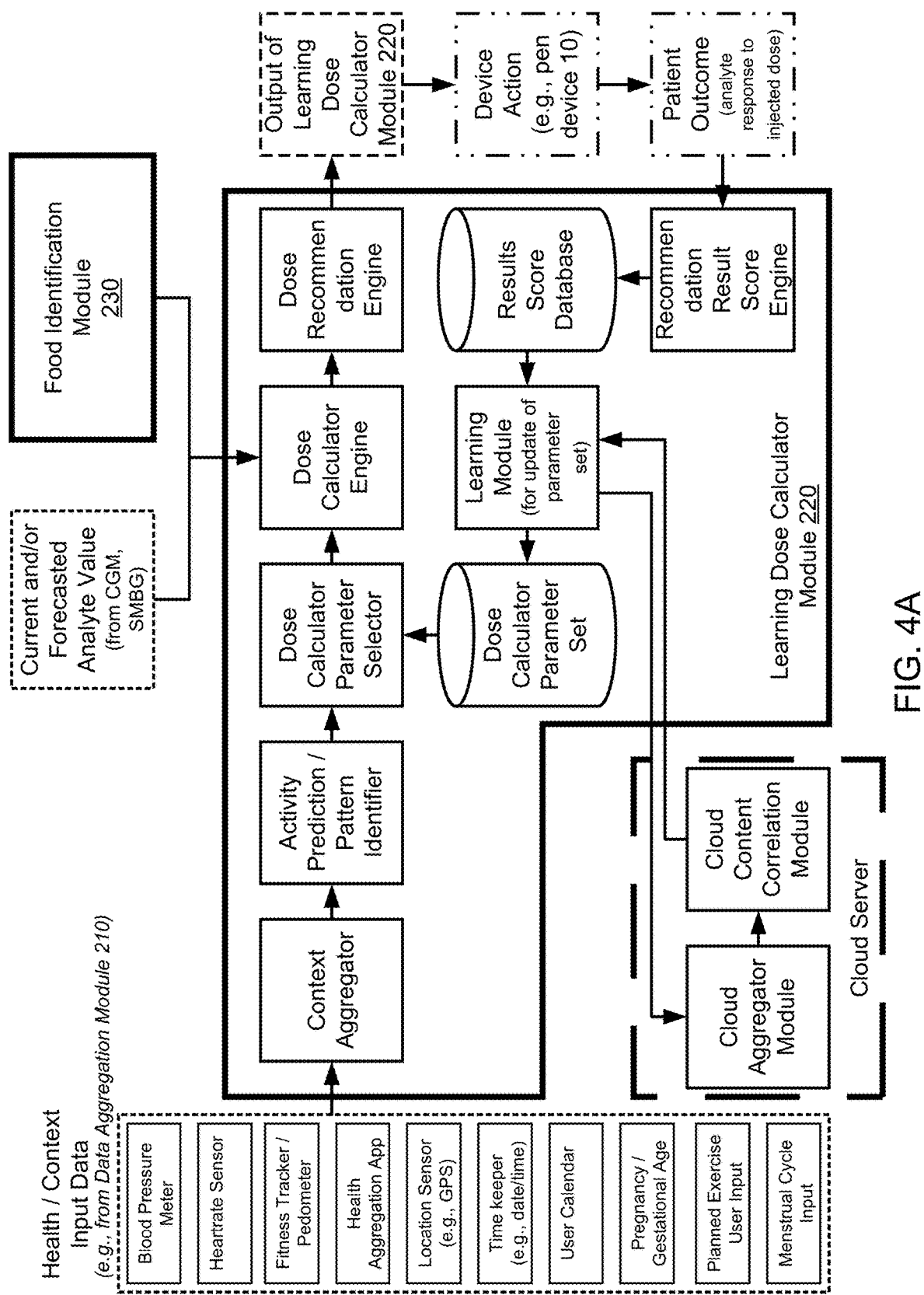
FIG. 4A shows a diagram illustrating a data flow and processing method implementable by the learning dose calculator module in accordance with some example embodiments of the intelligent medicine administration system.

FIG. 4A shows a diagram illustrating a data flow and processing method implementable by the learning dose calculator module 220. The learning dose calculator module 220 includes an organization of sub-modules and processing engines to manage intake, processing, storage and output of data. In the example embodiment shown in FIG. 4A, the learning dose calculator module 220 includes a context aggregator configured to receive health data and/or user contextual data, e.g., via the data aggregator module 210. In some implementations, the context aggregator can sort, flag, identify or otherwise organize the received health data and/or contextual data, which can include modifying the data to reflect a sorting code, flag, or identification by the context aggregator. The learning dose calculator module 220 includes an activity prediction/pattern identifier engine in data communication with the context aggregator and configured to process the received health data and/or contextual data to identify specific patterns associated with user activity, including user's physical activity (e.g., exercise, motion or other calorie consuming physical activity), event activity (e.g., participation at certain activities, etc.), and health activity (e.g., use of medications, heart rate, blood pressure, menstruation or pregnancy state, etc.). The learning dose calculator module 220 includes a dose calculator parameter selector in data communication with the pattern identifier engine and configured to select parameters for dose calculation, such as dosing parameters and clinical parameters, such as carb factor. In some implementations, the dose calculator parameter selector refers to a dose calculator parameter set database, which can be resident on the app and/or in the cloud, in conjunction with the current data from the pattern identifier engine. The learning dose calculator module 220 includes a dose calculator engine to receive parameters (e.g., from the dose calculator parameter selector) and/or data and make a particular calculation for a medicine dose which can be recommended for the patient at a particular point in time, based on the received information. In some implementations, the dose calculator engine can receive data from the food identification module 230, e.g., output from the module 230, and/or data directly from the data aggregator module 210, such as current and/or forecasted analyte values (e.g., from the sensor device 50, such as CGM or SMBG devices). The learning dose calculator module 220 includes a dose recommendation engine, in data communication with the dose calculator engine, to process the calculated dose of the medicine and determine whether to generate a recommendation of the calculated dose and produce an output of the recommendation accordingly. In some implementations, for example, the recommended calculated dose output can be displayed on an output of the companion device 5 or pen device 10; and additionally or alternatively, the recommended calculated dose output can be formatted as an instruction or executable to cause the pen device 10 to actuate a function, such as dial a specific dose (i.e., the calculated dose), dispense the specific dose, and/or alert the user to operate the pen device 10 for injection of the specific dose. Also, for example, the dose recommendation engine may suggest user actions other than an insulin dose, such as exercise to lower BG in lieu of insulin, food to raise BG, or taking no action.

The learning dose calculator module 220 includes a recommendation result score engine configured to receive data associated with an outcome of an implementation of the pen device 10 and/or companion device 5 based on the recommended calculated dose output. The received data can be updated analyte data, e.g., provided by the sensor device 50 via the data aggregator module 210, that is indicative of a physiological response of the patient to injection of the calculated dose (or lack of injection). The learning dose calculator module 230 includes a results score database in communication with the recommendation result score engine and configured to store the result scores. For example, the results score database can be resident on the companion device 5, e.g., as part of the app, and/or resident in the cloud. The learning dose calculator module 220 includes a learning module in communication with the results score database and configured to perform machine learning to optimize dose calculation parameters, e.g., stored by the dose calculator parameter set database, and update accordingly.

By comparing the actual outcome of a dose with the expected or predicted outcome, the dose setting parameters used for dose calculation can be tuned for the particular user, and for the particular context. For example, if an insulin dose lowers BG more than expected, the Insulin Sensitivity Factor (ISF) may be increased. Also, for example, by comparing behavior with similar contexts, e.g. doses taken after exercise, the dose setting parameters may be similarly adjusted specific to various contexts to improve future calculation accuracy. This can be evaluated and updated after a single dose, and/or in some implementations, for example, based on statistical analysis of a set of data from multiple doses.

The learning dose calculator module 220 is able to learn from past dosing outcomes (and/or food consumption outcomes and behavioral outcomes, like exercise) that are specific to each patient user of the system 100 by processing, e.g., statistically analyzing, at the learning module, (i) the results of a particular dosing and/or food consumption and/or activity event with (ii) the past dose setting parameters and (iii) the user's analyte state, health state and context data that were current at the time of the particular dosing and/or food consumption and/or activity event. From this analysis, the patient user's individual and holistic physiological response to the medicinal dosing (and/or food consumption or activity behavior) is quantified so that the system 100 can continuously optimize parameters that govern dose determination for specific situations the patient user finds himself/herself in, while also adapting to the changes that every person undergoes in life (e.g., such as a change in health through acute and chronic disease, stress level, diet, lifestyle changes, etc.).

In some implementations, for example, a cloud aggregator module and cloud content correlation module, resident on a cloud server as part of the system 100, is in communication with the learning dose calculator module 220 to inform learning module of processed parameters which may be associated with the patient's historical data, and/or data of other users with similar medical conditions, demographics, activities patterns, general health, etc.

Figure 4B:
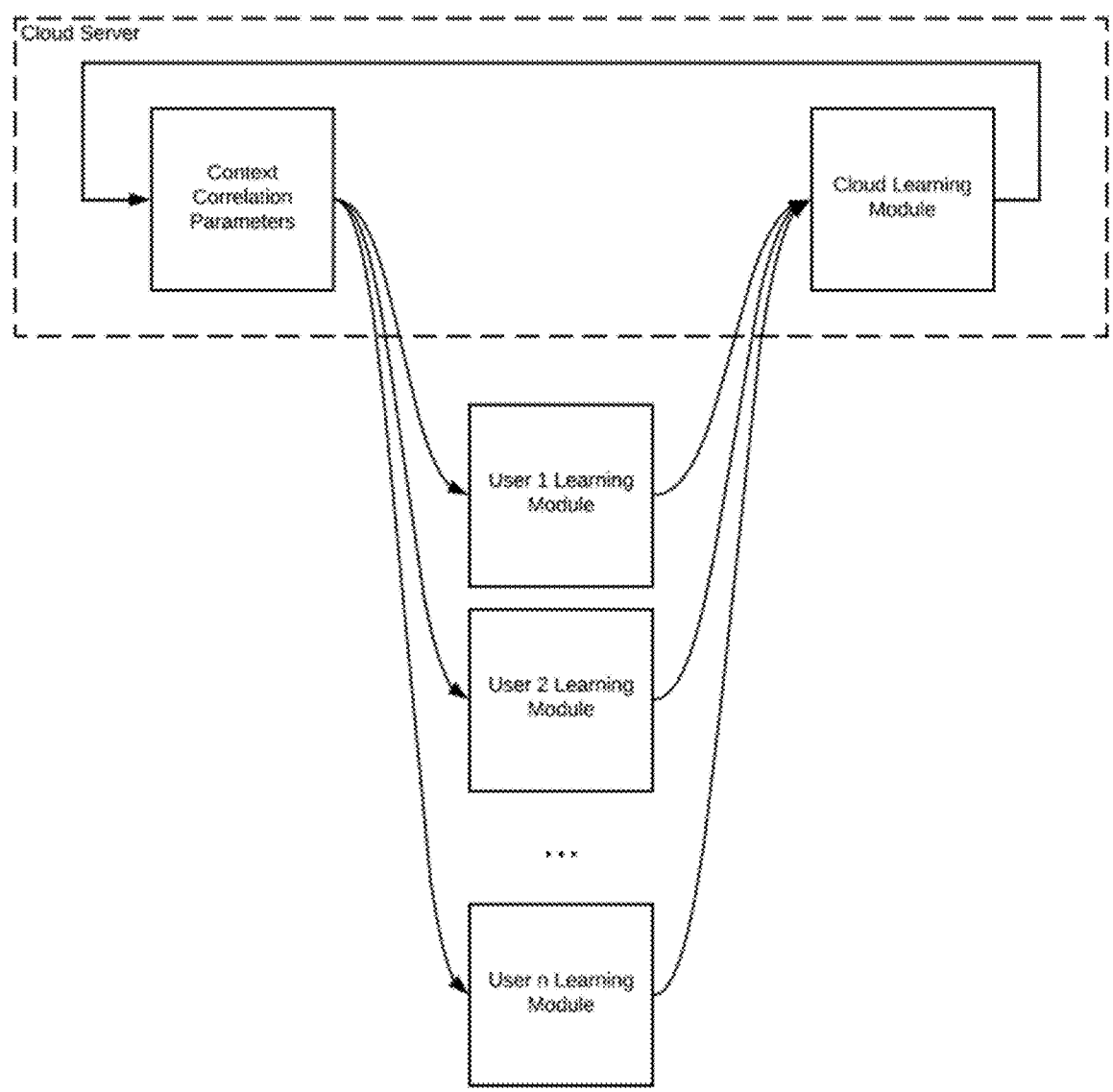
FIG. 4B shows a diagram illustrating a data flow and processing method implementable by a crowdsourced learning dose calculator module in accordance with some example embodiments of the intelligent medicine administration system.

FIG. 4B shows a diagram illustrating a data flow and processing method implementable by a crowdsourced learning dose calculator module in accordance with some example embodiments of the intelligent medicine administration system. In the example shown in FIG. 4B, the crowdsourced learning dose calculator can be implemented in the cloud (e.g., on the cloud server) and configured to receive data from user devices of the system 100, including the health data and contextual data and dose calculator parameter settings associated with a plurality of users. In some implementations, the crowdsourced learning dose calculator module is able to aggregate such health, contextual and dose calculator parameter settings data from the plurality of users of the system 100 to produce training sets that feed machine learning by the crowdsourced learning dose calculator module that identifies unrecognizable trends associated with sub-populations of the users. The outputs generated by the crowdsourced learning dose calculator module in the cloud include updated parameter settings that can be pushed down to certain selected patient users to modify their respective individual parameter settings, if determined necessary, when processed in conjunction with the specific individual patient user's learning dose calculator module 220, i.e., by the learning module of their device.

By analyzing trends in a large population of users, meal estimations and calculation parameters can be made more accurate. For example, if a specific food item or type of food has a greater than expected effect on BG based on the published grams of carbs, this can be incorporated into future calculations even for users who had never had this food before. Also, if a particular type of food (e.g., pizza) has a slower and longer BG response than typical other foods with similar carbs, this can be used to better forecast BG values used in dose calculations, or potentially to recommend a split bolus to spread out the insulin response to better match the food and normalize BG levels. In another example, contextual information may be evaluated across the population to infer their general effect on users. For example, the effects of exercise, pregnancy, stress, or heart-rate on dose calculator parameters can be inferred from a population and used to inform individuals' dose calculation parameters.

The crowdsourcing of food data associated with users of the system 100 can produce a database of crowdsourced food history data that includes of individual physiological response data to specific medicine doses associated with consumption of specific food items for a plurality of individual users. As an illustrative example, crowdsourcing the blood glucose response of users to food, such as recording that pepperoni pizza is listed as 30 carbs per slice but some of the users undergo a physiological response (e.g., glucose level response) to the pepperoni pizza having 30 carbs as if it had 40 grams per slice. In such a case, the crowdsourcing of food data can allow the system 100 to more accurately predict the BG response to a given food on an individualized basis from the population data. As such, the system 100 can better estimate carbs, and improve the accuracy of future dose calculations for all patient users of the system.

Figure 4C:
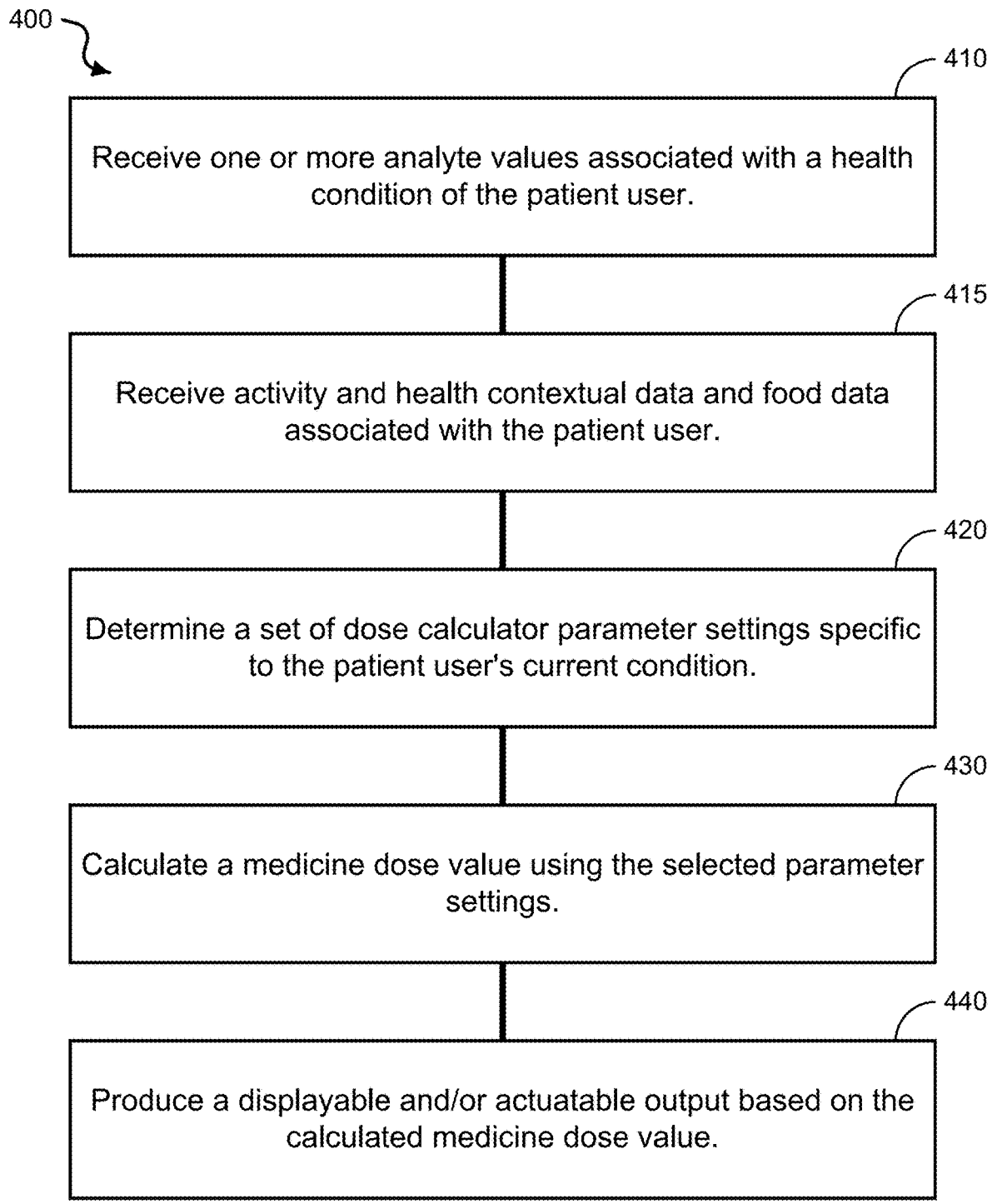
FIG. 4C shows a flow diagram of an example embodiment of a method for determining a dose of a medicine for a patient user, using the learning dose calculator module, in accordance with some embodiments of the disclosed technology.

FIG. 4C shows a flow diagram of a method 400 for determining a dose of a medicine for a patient user, using the learning dose calculator module 220 of the system 100, in accordance with some embodiments of the disclosed technology. The method 400 includes a process 410 to receive, at the learning dose calculator module 220 (e.g., via the data aggregator module 210 of the app on the companion device 5), one or more analyte values (e.g., current and/or historical glucose values) associated with a health condition (e.g., diabetes) of the patient user. In some implementations of the process 410, for example, one or more glucose values can be received by the sensor device 50, such as the example CGM or connected BG device. The method 400 includes a process 415 to receive, at the learning dose calculator module 220, (i) contextual data associated with activity and health status of the patient user that includes blood pressure, heartrate, menstrual and/or pregnancy state, movement tracking, location, calendared events, etc.; and (ii) food data associated with meal consumption, timing and nutrition, such as the amount of carbohydrates, which can be provided by the food identification module 230. In some implementations, for example, the food data can include general information about food aggregated and/or analyzed by the food identification module 230 for the learning dose calculator module 220 to process in generating recommendations to the patient user.

The method 400 includes a process 420 to determine, by the learning dose calculator module 220, a set of dose calculator parameter settings specific to the patient user's current condition. In implementations of the process 420, for example, the learning dose calculator module 220 can process the analyte, activity and health context, and food data to identify a certain pattern or set of estimated patterns associated with the user at the current time and state; and process the pattern or pattern set with a stored set of dose calculator parameters to select which parameter settings should be used in a current dose calculation. The method 400 includes a process 430 to calculate, by the learning dose calculator module 220, a medicine dose value using the selected parameter settings. Implementations of the processes 410-430 can be autonomous and continuous, e.g., periodically and/or intermittently updating and executing.

The method 400 includes a process 440 to produce an output based on the calculated medicine dose value. In some implementations of the process 440, for example, the output includes an executable to display, on a display component of the companion device 5 or the pen device 10, the calculated dose of the medicine. In some implementations of the process 440, for example, the output includes an executable to cause the pen device 10 to actuate a function, such as automatically set (e.g., dial) the calculated dose by the dose setting mechanism of the pen device 10, automatically dispense the calculated dose by the dose dispensing mechanism of the pen device 10, and/or alert the user to operate the pen device 10 for injection of the calculated dose by a display component of the pen device 10. Notably, for example, automatic dispensing by the dose dispensing mechanism can include automatically setting the calculated dose and waiting for user approval to cause semi-automatic actuation of the dispensing when the user has injected the needle to the appropriate location of their body. Also, for example, actuation of alerts can also or alternatively be implemented by the app of the companion device 5.

Figure 4D:
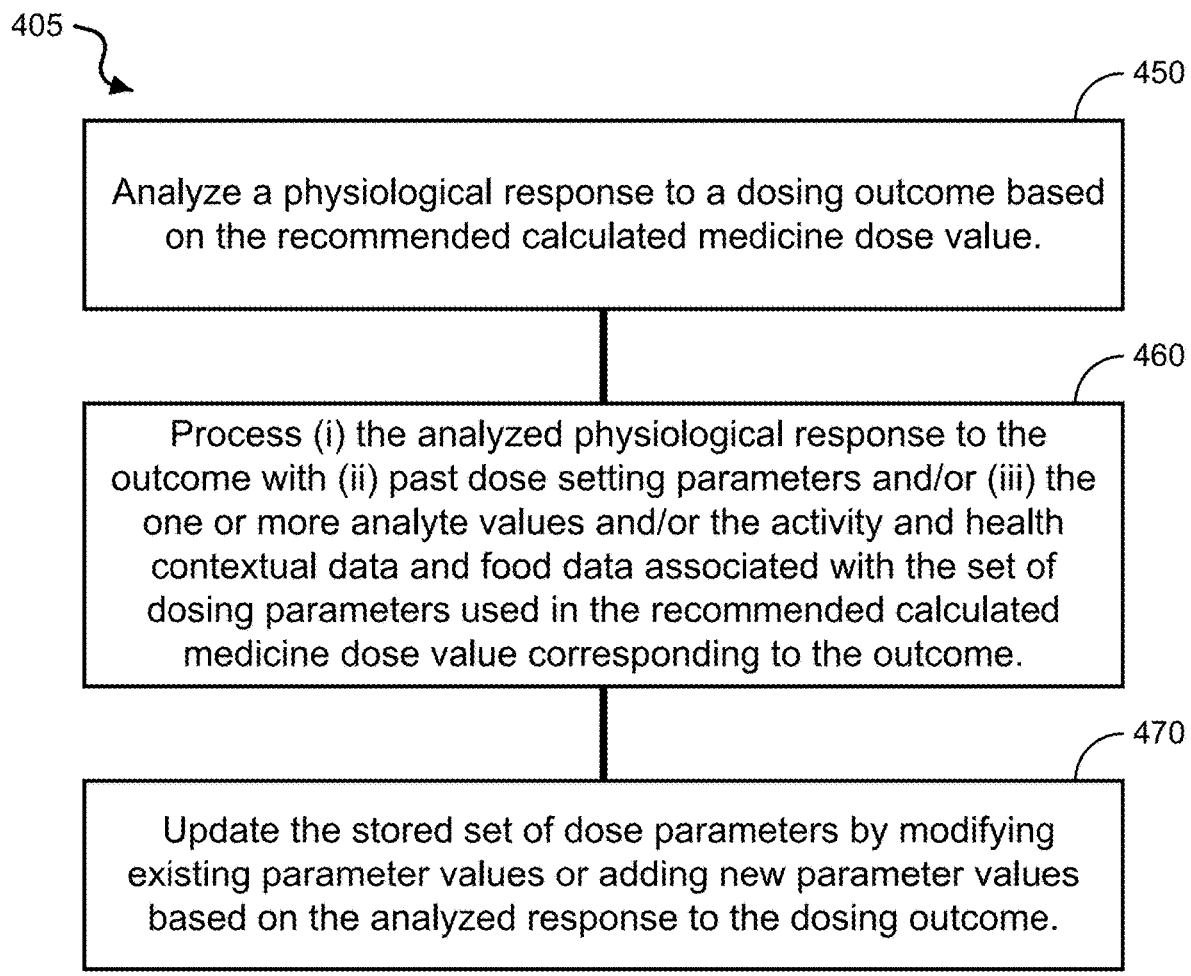
FIG. 4D shows a diagram of an example embodiment of a method for adaptively optimizing dose setting parameters, which may be looped into the method of FIG. 4C.

In some embodiments, the method 400 may further include or alternatively include one or more of the following processes and features. FIG. 4D shows a diagram of a method 405 for adaptively optimizing dose setting parameters, using the learning dose calculator module 220 of the system 100, which can be looped into the method 400 for determining a dose of a medicine for a patient user, in accordance with some embodiments of the disclosed technology. For example, after a dosing event using the recommended dose calculated in the method 400 and/or other event that may result in a physiological response associated with a monitored analyte of the patient user, the method 405 can analyze data associated with the outcome of the event for optimizing the dose calculator parameter settings for a future dose calculation implemented using the method 400.

The method 405 includes a process 450 for the learning dose calculator module 220 to analyze the outcome of the recommended calculated dose, i.e., analyze implementation of the output displayed and/or actuated. For example, the learning dose calculator module 220 can generate a quantitative score associated with a result, e.g., time-stamped to the score and/or tagged to certain data used in the analysis to generate the score. The method 405 includes a process 460 for the learning dose calculator module 220 to process, e.g., statistically analyze, (i) the analyzed physiological response to the outcome from the process 450 with (ii) the past dose setting parameters selected at the process 420 and/or (iii) the one or more analyte values and/or the activity and health contextual data and food data received at the processes 410 and 415 that are associated with the recommended medicine dose value calculated at the process 430, e.g., which may correspond to the outcome. For example, in implementations, the process 460 can produce a new set of dose setting parameters with respect to the set or sets of dose setting parameters already stored and/or modify one or more specific parameters within a set or sets of dose setting parameters already stored. The method 405 includes a process 470 for the learning dose calculator module 220 to update the stored set of dose parameters by modifying existing parameter values or adding new parameter values based on the analyzed outcomes. For example, the learning dose calculator module 220 can determine one or more metric values associated with the medicine delivered by the pen device 10. An illustrative example includes the learning dose calculator module 220 generating a metric value of the amount of 'active medicine' in the body of the patient user, e.g., such as insulin on board (IOB) for insulin treatment. In some implementations of the process 460, some of the dose setting parameters may be imported from other health applications operable on the companion device 5, such as values associated with the monitored analyte by the sensor device 50 or from another medicine delivery device (e.g., insulin pump). As an example, a current IOB value can be imported by the software app associated from the sensor device 50 and compared, by the learning submodule of the learning dose calculator module 220, to the present IOB value stored and/or generated by the app of the system 100. Both may be stored, or one may be substituted for the other. Likewise, some of the dose setting parameters can be received by the app from a health aggregation app, such as Apple Healthkit or Google Health or the like).

In some implementations, for example, the method 400 includes a process for autonomously determining an amount of carbohydrates or calories to be recommended for intake (ingestion) by the patient user; and displaying the determined amount of carbohydrates or calories to the user via the companion device 5. In some implementations, for example, the method 400 includes a process for determining a subtype of the medicine to be dispensed by the injection pen device 10, in which different subtypes of the medicine differ in one or both of pharmacokinetics (PK) and pharmacodynamics (PD) of the medicine, and autonomously calculating the dose is further based on a PK-PD profile of the subtype of the medicine.

Food Identification

In some example embodiments of the app resident on the companion device 5, the food identification module 230 is configured to aggregate and process contextual data pertaining to food and food intake by the patient user, in which the processed data can be provided to the learning dose calculator to calculate a time-relevant and circumstance-relevant dose amount that the system recommends to the patient to dose. The food identification module 230 can be executed, by the app, in compilation with the learning dose calculator module 220 to provide more specific and accurate information about food intake (e.g., carbs) based on user location, food history, image recognition, and/or 'crowd-sourced' nutritional content and effects of certain foods. The food identification module 230 allows for passive input of food/carb-related data to the learning dose calculator module 220.

In some implementations, for example, the food identification module 230 is configured to allow entry of (e.g., pull) information pertaining to specific foods and/or specific restaurant menu items, e.g., rather than just carbs for use in a dose calculator. In some implementations, the system includes the information in a central database of nutritional information, which the app can reference. For example, location (e.g., at home, or at a specific restaurant) could be used to intelligently offer a short list of food items to choose from, or could help improve accuracy of image recognition. Highest probability foods (e.g., based on recent history and other contextual factors) can be quickly accessible for selection, also intelligently filtered based on location and time of day (which meal). Multiple nutrition databases could be referenced, and either averaged or the most conservative value could be used.

Figure 5A:
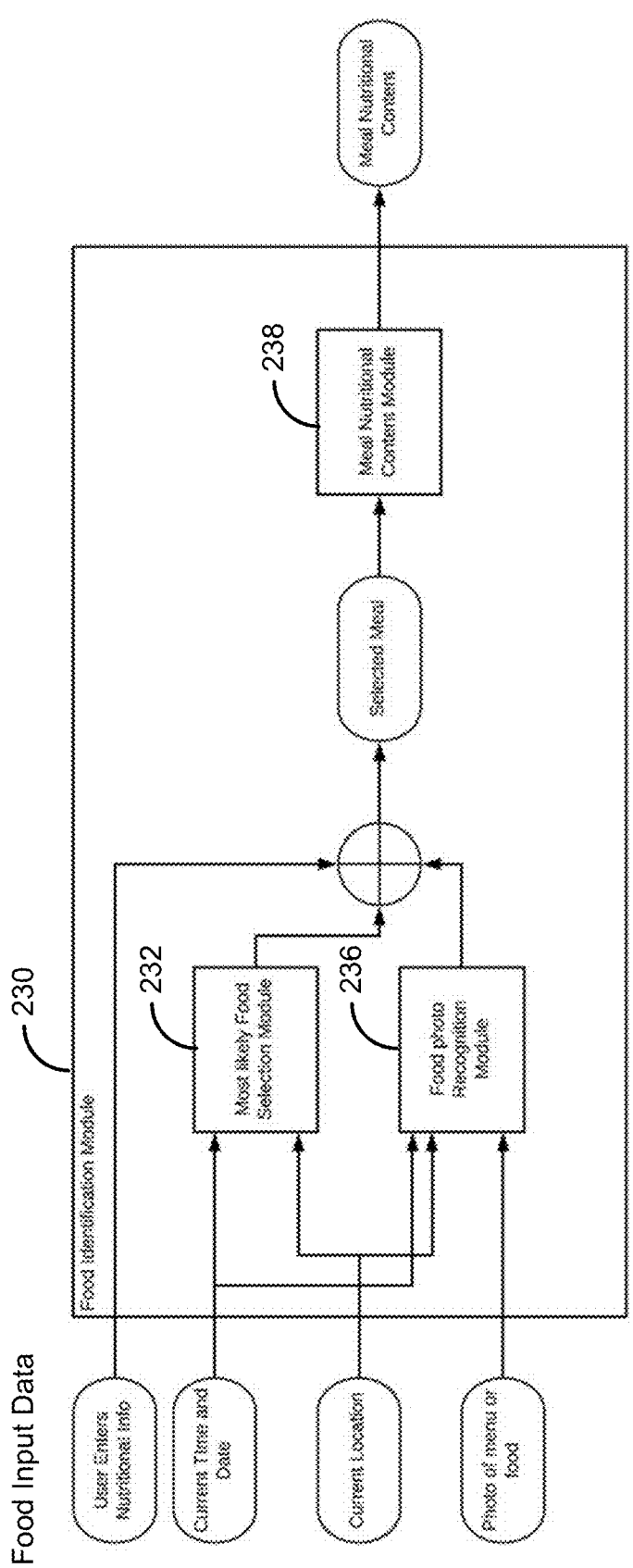
FIGS. 5A-5D show diagrams illustrating a data flow and processing method implementable by a food identification module in accordance with some example embodiments of the intelligent medicine administration system.
Figure 5B:
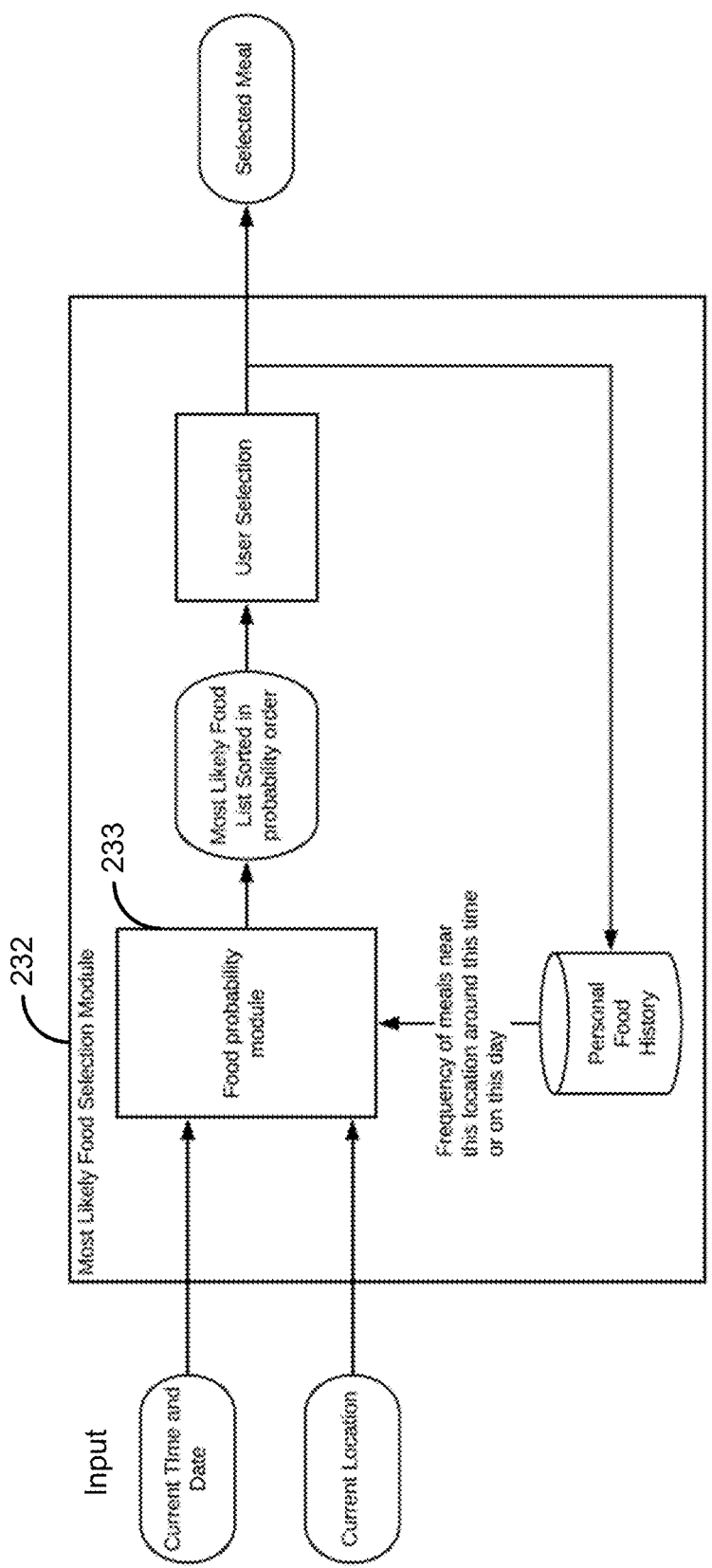
Figure 5C:
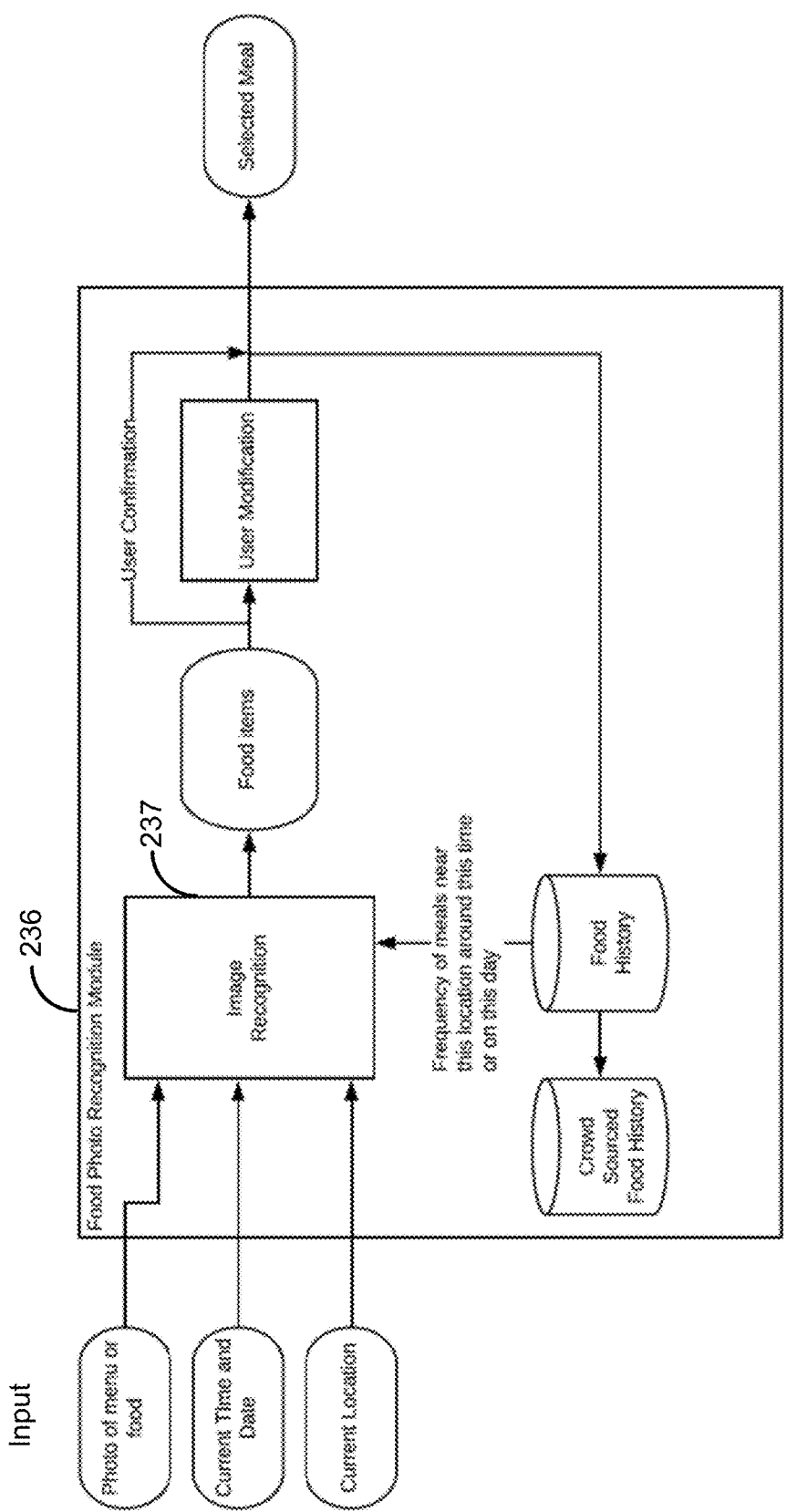
Figure 5D:
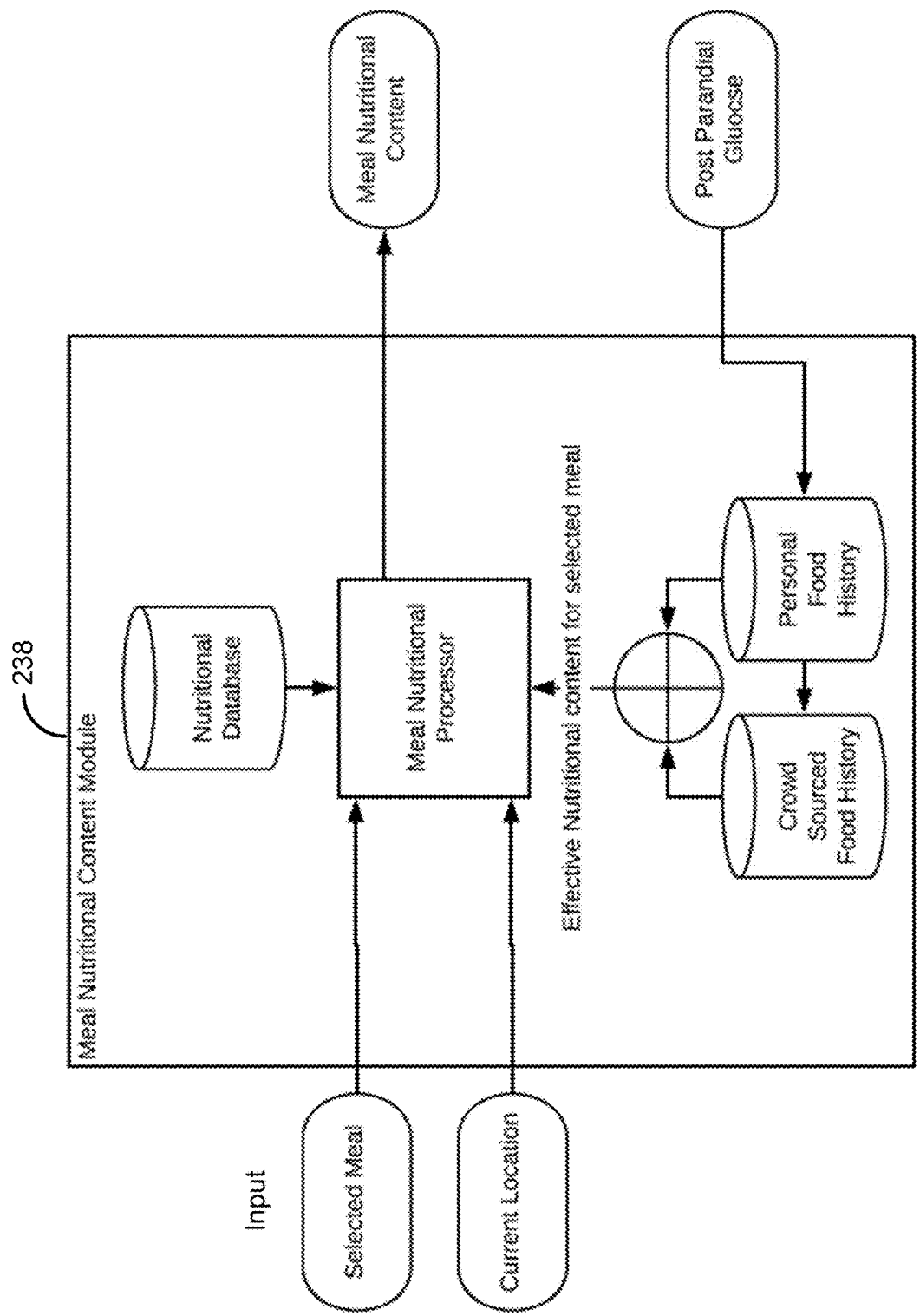

FIGS. 5A-5D show diagrams illustrating a data flow and processing method implementable by the food identification module 230. The food identification module 230 includes an organization of sub-modules and processing engines to manage intake, processing, storage and output of data. As shown in FIG. 5A, the food identification module 230 includes a most-likely food selection module 232, a food-photo recognition module 236 and a meal-nutritional content module 238 in data communication to process food data inputs, e.g., including user entries on nutritional information about food, current time and date, current location of the user, and/or images of food or a menu item, to produce a food data output associated with meal nutrition content that can be used by the learning dose calculator module 220. As shown in FIGS. 5A and 5B, the most-likely food selection module 232 is configured to receive current time and date and current location input data, e.g., via the data aggregator module 210; and as shown in FIGS. 5A and 5C, the food-photo recognition module 236 is configured to receive current time and date, current location and food or menu item image input data. As shown in FIGS. 5A and 5D, an intermediary output identifying a selected meal is provided to the meal-nutritional content module 238 which processes the selected meal (which may include some input data) to provide the food data output associated with meal nutrition content.

Referring to FIG. 5B, the most-likely food selection module 232 includes a food probability module 233 that processes the inputs with food intake history data, such as the user's individual food history and/or frequency of meals at or near the location and/or time of food consumption, and the food probability module 233 generates a sorted list of food type (e.g., which can include a tag or link to stored nutrition and other associated data) based on probability analysis. In some implementations, the generated sorted list can be displayed (e.g., on the companion device 5) so that the patient user can select the particular meal he/she will consume or has consumed. Notably, the selection of the meal may also be based on the processing implemented by the food-photo recognition module 236, and/or with user inputted information about the meal (as shown in FIG. 5A). The sorted list of food and/or a user-selection of a food from the list can be stored in the food history database, e.g., for future references. In some implementations, the most-likely food selection module 232 may automatically select the meal based on the probability results (e.g., high likelihood of one type of food compared to others on the list) and/or if the user does not provide feedback on a selected meal.

Referring to FIG. 5C, the food-photo recognition module 236 includes an image recognition module 237 that receives the inputs and identifies food items from the inputted image based on the current time and date and current location in conjunction with food history data. The image recognition module 237 can execute image recognition algorithms to determine properties of the food including type, size, preparation level, etc. In some implementations, the identified food item from the processed image can be displayed (e.g., on the companion device 5) so that the patient user can confirm or modify the identification of the particular food item he/she may consume or did consumed. The identified food item can be processed with the food item sorted list by the most-likely food selection module 232, and/or with user inputted information about the meal (as shown in FIG. 5A), to determine the selected meal. The identified food item from the processed image and/or a user-confirmation or modification of the food item from the processed image can be stored in the food history database, e.g., for future references. Similarly, this data can be provided to a crowd-sourced food history database, e.g., stored in the cloud.

Referring to FIG. 5D, the meal nutritional content module 238 includes a meal nutritional processing engine that processes the selected meal (output from the most-likely food selection module 232 and/or the food-photo recognition module 236) with one or more input data (e.g., current location) and food history data to produce the meal nutritional content output, which can be provided to the learning dose calculator module 220. In some implementations, the patient outcome data provided to the learning dose calculator module 220 may also be provided to the food identification module 230 to augment the food history database, e.g., such as with post-prandial glucose measurements associated with consumption of certain foods by individual patient users.

In some implementations, image recognition software could be used to identify food about to be eaten from a picture taken with the camera. The output of image recognition software in combination with a food database can produce the actual nutritional content of food automatically. The food identification module 230 can input such information for processing and/or providing to the learning dose calculator module 220. In an illustrative example, the companion device 5 can be used to allow the user to take a picture of a menu listing of an item that he/she is eating, in which the app can OCR (e.g., utilize Optical Character Recognition to analyze) the image to determine what the user is eating and then correlate that with the food database. This is an example of a photo of menu listing, as opposed to a photo of food itself.

The food identification module 230 can include a list of food information that can be compared to 'usual meals', e.g., to improve accuracy. Nutritional content can be used to inform the carb entry to the learning dose calculator module 220. As illustrative example, nutritional content can also inform recommended timing of doses, such as recommending a second correction dose an hour after a meal with low glycemic index foods (e.g. pizza).

Regarding food portion selection—one challenge with food estimation is portion size. For example, should a user have 1 cup of rice vs 2 cups, etc. The results from a food database search can return nutritional information based upon a standard measure (e.g., 1 cup rice=14 g carbs). The user interface of the app can be configured to allow the user to change the portion size of the food result. The user can select the portion units (e.g., g, lbs., small bowl, etc.). The portion sizes can be conveyed in physical units the user can relate to relative sizes (e.g., golf ball size, baseball size, softball size, football size, etc.).

In implementations of the food identification module 230, for example, the user's location, and/or meal history near that location can be used as meta data into the image recognition algorithm to increase accuracy of results. The user's location, and/or meal history near that location can be used with a fuzzy scoring algorithm to rank results on top of ranked results returned from the image recognition algorithm results. In some implementations, for example, undesired results of the image matching algorithm can be filtered by a weighted matching filter. For example, if categories are returned as matches, such as "food" or "lunch" but are not foods, a weighted matching algorithm can look for exact results or nearly exact results matching that description and filtered out of the results before sending to the user or into a food database search. The results of the image recognition algorithm may use different terms than the inputs to a food database. One, several or all of the terms from a result from the image recognition algorithm may be used to search the food database. Results from possible matches from the food database search may be returned, of which the software must select the results to display to the user. The fuzzy matching algorithm can be used to compare the input of the search to the output of the food database search and score the results. For example, the app can display, via the display of the companion device 5, the highest scoring result or results. The output of the food database search from one image recognition result can be compared to the output of the other food database searches from the other image recognition result, and highest frequency results scored higher, resulting in a higher ranking of display to the user.

The follow is an illustrative example of an image analysis implementation by the example image recognition algorithm. If the image recognition algorithm determines there is a hamburger in the image, and the present time is lunchtime and the patient user is at a particular fast food restaurant, such as McDonald's, and that user had a Big Mac two weeks ago, for example, the image recognition algorithm will be able to determine that the food item in the picture is a Big Mac hamburger with a high degree of confidence, e.g., a particular type of food item with more specificity. In some implementations, the app can provide the determined suggestion to the user for confirmation, and/or top suggestions that may include McDonalds hamburger items. Also, for example, if the same image is taken at 6 am at a donut shop, even if "donut" was lower on the list of possible image recognition results, it will be given more consideration in this instance based on the additional contextual information, e.g., assigned a higher probability, than in the first scenario, due to the additional situational inputs.

An example embodiment of a food image recognition and analysis method includes receiving an image of a food item, e.g., which can be captured by the camera device and inputted by the data aggregator module of the app. The method includes receiving an interpreted data set providing a list of likely food matches and their associated information (e.g., calories, carb content, etc.). Additionally or alternatively, for example, the image recognition algorithm can process the image itself to provide or augment the data set providing the list of likely food matches, in some implementations. The method includes processing the data set to assign a confidence value or weight to each food item listed in the data set (e.g., 0.000 to 1.000) based on analysis of the contextual data specific to the patient user and/or a population of patient users. In some implementations to assign a confidence value or weight, for example, items in (or similar to) the patient user's previous food log history are assigned higher probability than foods they've never logged. This can be proportional, like 1.0 for foods previously logged, a 0.8 for foods similar to foods previously logged, 0.2 for foods outside the patient user's normal eating habits. In some implementations, for example, a similar routine could be done by localization or language too, especially for a new user who hasn't logged much yet—for example, people in Texas might receive different weightings than people in Thailand. In some implementations to assign a confidence value or weight, for example, location is used to see if the user is at a restaurant or at home, or another location. For example, items sold at the patient user's location might be weighted 1.0, and items sold within 1 mile might be weighted 0.7. Or at home, fast food items might be weighted 0.2 but home cooked and store-bought foods would be weighted higher, e.g., 1.0. In some implementations to assign a confidence value or weight, for example, time of day is used in processing. For example, perhaps at 8 am an omelet would be weighted 1.0 but meatloaf might be ranked 0.2. This could be based on known meal types for foods, and/or the patient user's own history of when certain meals were eaten. When all these (and other) factors are considered, the probabilities are all multiplied together to give the overall most likely result. By contrast, a pure filtering algorithm might never identify a bagel being eaten at night, but with a "fuzzy" scoring algorithm as in the example food identification module 230, even if its time-of-day probability is low, if the other probabilities are high enough the correct identification can still be made. In some implementations, the image recognition algorithm can process a list more specific to the patient user, such as the patient user's own meal history, and then use the image to identify which on the list is the most likely match.

In some implementations, the food image recognition and analysis method includes providing the identified food item and the corresponding information to the learning dose calculator. In some implementations, the method includes providing the confidence-ranked list (or partial list of the top-ranked items) of food items to the patient user to prompt a user input, such as a confirmation and/or an adjustment. For example, there may still not be perfect identification or measurement of portion size, so the user could still be presented with the top few suggestions and an ability to adjust portion size.

In some implementations, the food image recognition and analysis method includes manual filtering. For example, perhaps the user explicitly selects the restaurant or type of meal or food group so that only those types of results are returned. Or they may verbally state what they are eating so that a voice recognition result could be added as an additional factor for filtering or weighting.

In some implementations, classification algorithms can be executed on image recognition search results, as an input to the food database search, to enhance food database search accuracy. For example, if the image recognition software returns "grape" or a picture of grapes, but the term used in the food database is "grapes, raw", a classification algorithm can be used upon search results to add or modify the food database search inputs to improve results.

The patient user's location and/or meal history near that location can be used as meta data into the food database search algorithm to increase accuracy of results be used to score results and improve accuracy of result rankings. In case of ambiguity, the user could be prompted to confirm or select between the most likely matches. The patient's recent meal history (e.g., in the past 4 hours) can further be used to improve accuracy as well. For example if the patient just ate a large meal, it may be more likely that a photo soon after would be of a snack or small dessert rather than a second large meal. Or if it is late in the afternoon when food would typically most likely be a snack, but the user has not yet eaten lunch, the algorithm may increase the probability of a lunch meal being identified.

As an example, the learning dose calculator module 220 may determine a bolus to be delivered intermittently over a period of time. For example, the determined dose may be staggered as partial-doses for certain foods with known slow glycemic response, such as pizza, and therefore prompt the patient user to dispense a partial correction dose immediately and the rest of the dose a time period or periods later to try to maintain a consistent, steady glucose response. Factors also included previous glucose response history, such as to certain foods at certain times of day and under certain conditions (e.g., a burrito on Tuesdays after work and exercise at the gym).

Parameter Setting

In examples of the system for insulin delivery, if a patient user of the system does not use a CGM device, the learning dose calculator module 220 may prompt for a blood glucose single measurement at specific times, e.g., after a known dose and/or meal to allow calculation of clinical parameters, such as carb factor. The app, e.g., using the learning dose calculator module 220, may passively monitor CGM data following insulin doses and logged meals and activity to determine the effect of insulin on a particular patient and calculate clinical parameters, such as carb factor. In some examples, after a physician gets a new patient started and estimates insulin parameters for that person, the results of the first days or weeks can be sent to the physician for review, and they may opt to modify the parameters based on the outcome. These modifications could be pushed wirelessly to the patient user's companion device 5 for the app, and they may confirm the updates. The first days or weeks could include normal use, as well as possibly controlled experiments with specific foods or other behaviors. For example, security features associated with parameter settings of a dose calculator, such as passcode or fingerprint detection, may be required for physician making changes. An example method for parameter setting can include setting initial parameters on the app; collecting data by the app; calculating parameters for optimal conditions specific to the patient user in the dose calculator; providing updated recommendation associated with the parameters to physician, in which the physician approves or modifies the parameter setting; receiving, at the app, the approval and/or modification to the patient's companion device 5; and obtaining approval by the patient user.

Figure 6A:
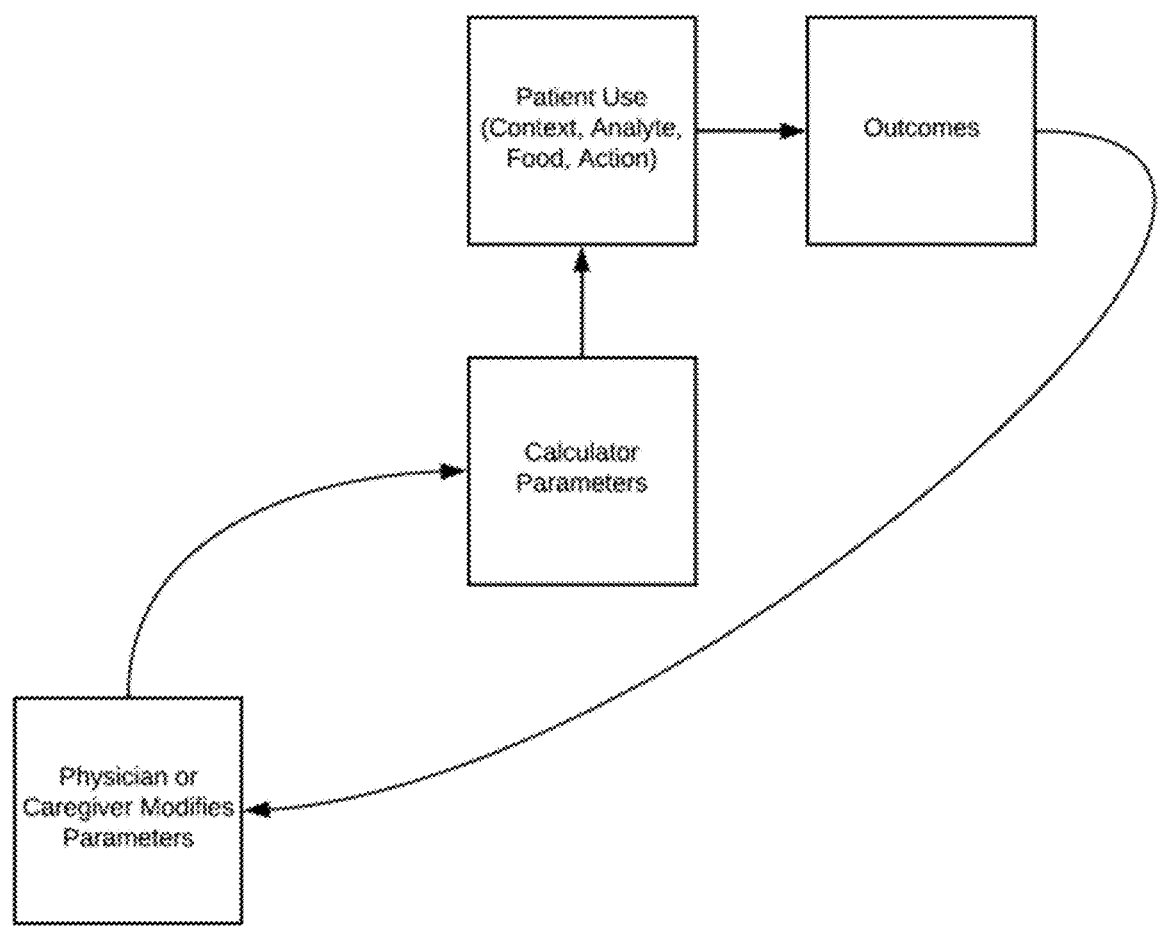
FIGS. 6A-6D show diagrams illustrating example implementations of parameter settings by the learning dose calculator module in accordance with some example embodiments of the intelligent medicine administration system.
Figure 6B:
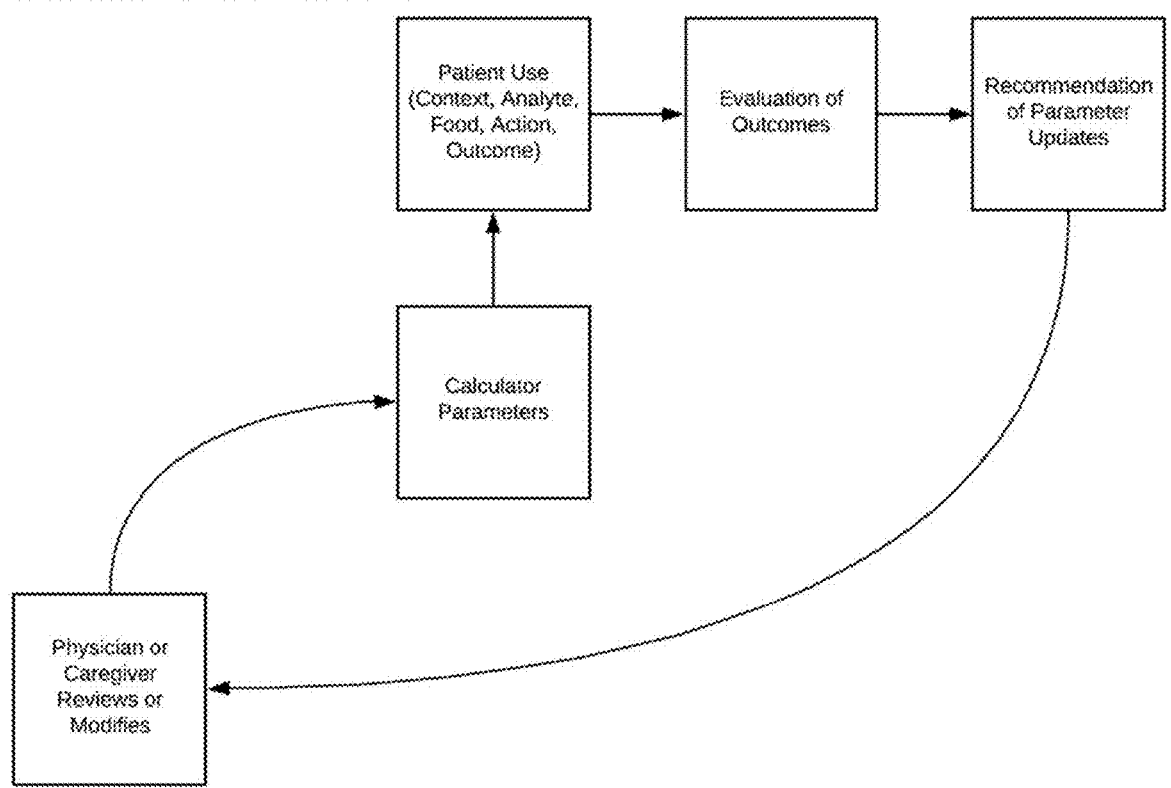
Figure 6C:
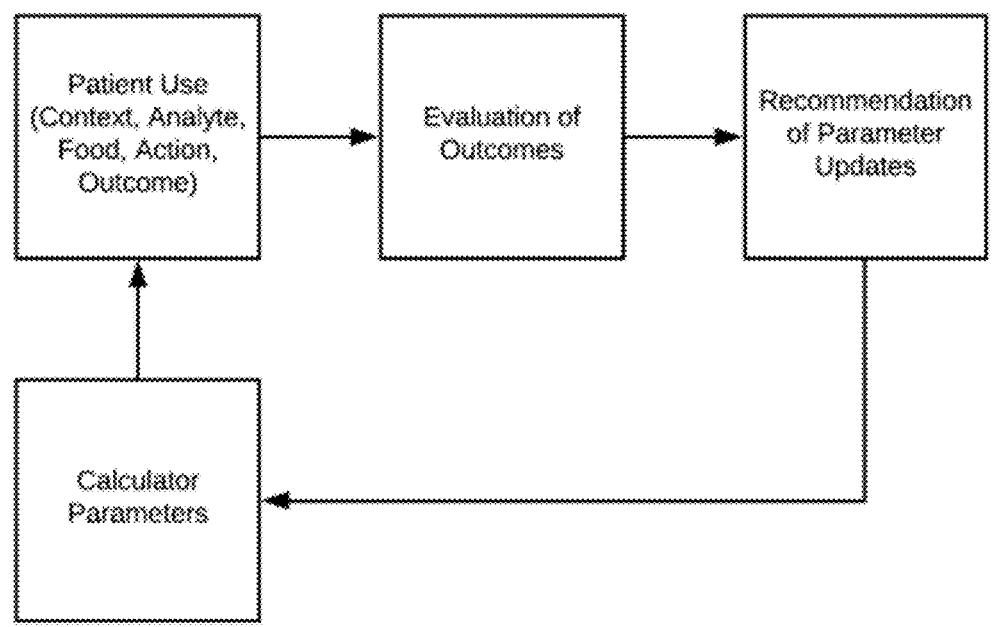
Figure 6D:
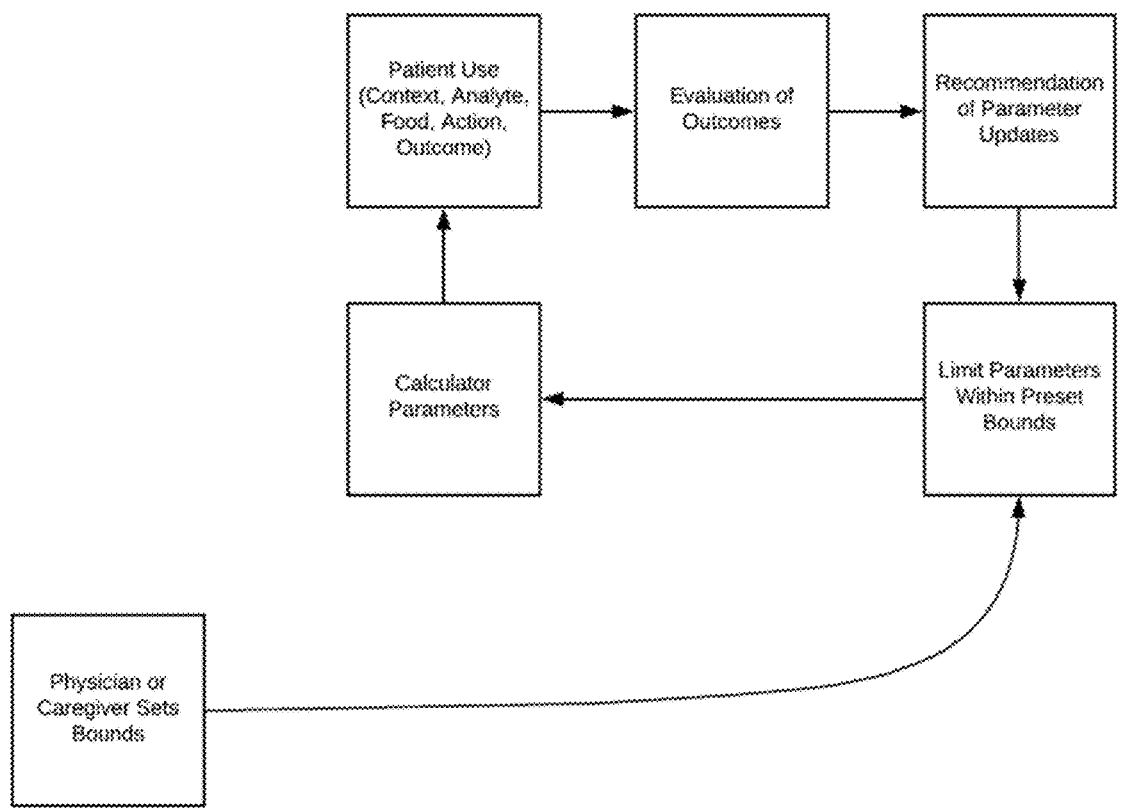

FIGS. 6A-6D show diagrams illustrating example implementations of parameter settings by the learning dose calculator module 220 and which can be remotely updated, e.g., via physician or caregiver, or fully or semi-automatically updated. The example shown in FIG. 6A shows a feedback loop of a fully manual dose calculator, in which operation of the learning dose calculator module 220 allows an external user, such as a HCP (e.g., physician, nurse, parent or qualified caregiver) or a patient, to remotely update dose calculator parameters. The example shown in FIG. 6B shows a feedback loop of a semi-automatic dose calculator with manual review nodes, in which operation of the learning dose calculator module 220 allows an external user, such as a HCP or patient, to remotely update dose calculator parameters based on evaluation of patient outcomes and the previously recommended parameters that may affect those outcomes. The example shown in FIG. 6C shows a feedback loop of a fully automatic dose calculator, in which operation of the learning dose calculator module 220 does not involve input by an external user, once implemented, and can automatically update dose calculator parameters based on evaluation of patient outcomes and the previously recommended parameters that may affect those outcomes. The example shown in FIG. 6C shows a feedback loop of a semi-automatic dose calculator, in which operation of the learning dose calculator module 220 provides an opportunity for input by an external user, once implemented, to limit parameters within preset bounds and allows for automatic updates of dose calculator parameters based on evaluation of patient outcomes and the previously recommended parameters that may affect those outcomes.

In some implementations for gestational diabetes, for example, the app is configured to modify dosing parameters based on due date, or gestational age, which can be based on population trend of pregnancy effects (as pregnancy advances insulin resistance increases, especially in the 3rd trimester). For example, the app can include a setting (e.g., in the user interface of the learning dose calculator module 220) for people with diabetes who become pregnant, for adjusting parameters associated with being pregnant. The app can be configured to allow more intensive control, larger safety margin from hypoglycemic conditions, higher target glucose values, adjusted clinical parameters based on pregnancy effects, and others.

In some implementations, the app can manage controlled experiments to be performed by the patient user according to prescribed protocols to determine initial clinical parameters for a dose calculator. For example, specific meals could be chosen to evaluate different nutrient types (e.g., carbs, fatty foods, high protein, etc.), and/or high/low glycemic index foods, and or determine or characterize extreme values for the particular patient. In an illustrative example, the patient could be requested not to exercise and to fast for some time before the meal. Food could be pre-packaged and given to patients for the test, or common restaurant menu items (e.g., a McDonalds Big Mac) could be used that patients could get on their own. The controlled experiments could include exercise, in which the app prompts for specific activity and evaluate response. Any of the example activities of the controlled experiments can be combined with an insulin dose in evaluating the patient user's response.

Glucose Data in Analysis of Insulin Dose Calculation

Overall there is a desire to fine-tune insulin dosing to give patients a desired glucose response. To help with this, feedback of doses based on single blood glucose (BG) values or continuous glucose values (e.g., from CGM data) could be useful. Examples include reports, generated by the app, which show a short graph of BG or CGM data for a period before and after a dose was taken, and/or event based CGM or BG. In some implementations, the app can provide retrospective scoring the "success" of an insulin dose based on BG outcome after the dose, or comparing the BG status before and after the dose was taken and evaluating improvement, where the score is the percentage modification of the recommendation to achieve target. For example, a score of 0 is a perfect dose, and a score of 200 would increase the dose taken by 200%. The example score can be calculated by: modified dose amount/actual dose, where modified dose amount=(post prandial glucose−target glucose)/insulin sensitivity factor. In some implementations, the app, e.g., using the learning dose calculator module 220, can retroactively calculate and display what would have been the right dose of the insulin medication. In this manner, the patient user may be able to identify the context for more accurate dosing in future situations.

In some implementations, the app includes a logbook module, also referred to as the data aggregation module 210, which manages recording and organization of the health data and contextual data utilized by the modules of the app. In some examples, doses could be marked according to color, size, or symbols based on an evaluated "success" scoring (e.g., such as color-coded red, green, yellow based on success). Many doses over a long time period (e.g., weeks or months) can be evaluated and summarized for a report. The report could indicate relative success and identify low-success trends based on, e.g., meal or time of day, the size of the correction, whether or not the dose calculator was used, the type of food eaten, the type of activity logged, where the dose was taken (work, home, location of exercise), etc.

In some implementations of the learning dose calculator module 220, for example, the app separately calculates the portion of a dose that was for carb correction and the portion that was for glucose (e.g., BG) correction. Because of this, the "success" of the dose could be evaluated for both components separately.

In some implementations, for example, the app is configured to detect exercise (or abnormal exercise) and based on likely increased insulin sensitivity warn user of likely excess IOB which is likely to result in hypoglycemia.

In some implementations, for example, the app is configured to allow review of previous doses based on specific food type, showing qualitative "success" or graphical BG plots surrounding each one. For example, the app can allow the user to review what happened when the patient had a similar meal in the past to help inform the patient of the dose decision. For example, the app can allow the user to filter by where they currently are instead of food type. For instance, the app can indicate if the patient always goes high after visiting a particular restaurant.

Insulin Display

In example implementations of the pen device 10 used for insulin injections, for example, a processing unit of the pen device 10 may calculate the remaining insulin based on an absolute measurement of plunger position, or by tracking the amount of insulin used since the last cartridge replacement. This can be sent to the app to be displayed to the user to help them plan their day. In such examples, this can be more precise and more convenient than trying to visually estimate how much insulin is left in the pen. The app may also include provisions for prompting the user or automatically mail-ordering more insulin after a total known amount of usage to ensure the user does not run out. This could be based on a set threshold, or based on the average rate of insulin use to predict when the user's supply will be depleted.

Device Connection Ecosystem

In some embodiments, the system includes the app on the user's smart device (e.g., the patient user's smartphone) to connect to the user's multiple smart pens, caps, and/or pumps for a single patient user. Typically, patients of diabetes rely on multiple delivery devices for managing dosing of fast-acting insulin and long-acting insulin. Some embodiments of the intelligent medicine administration system include a device ecosystem connection module, e.g., of the app, that allows the user's multiple devices to wirelessly sync to each other and to the a central server in the cloud, to share health data (e.g., dose amounts, dosing parameters, analyte levels, contextual data, etc.) and device security data among some or all devices.

In some examples for the pen device 10 implemented for insulin delivery, the patient user may possess multiple insulin devices. The device ecosystem connection module can be implemented to wirelessly sync the companion device 5 to each of the other insulin devices, based on the capabilities of the insulin devices. When synced, the device ecosystem connection module allows the data and device setting parameters of the device to be accessible to other devices locally, and to a cloud server, thereby providing smart devices the capability to sync with a central data management server, which may be used by other device services including 3rd party servers (e.g., CGM for glucose monitoring and/or healthcare institutions). For example, data can be shared among all devices so that patient's IOB is known, as well as other clinical parameters such as food, exercise, and calculator settings.

The device ecosystem connection module can be implemented to wirelessly sync the pen device 10 to other pen devices that include a complimentary device ecosystem connection module. Similarly, the pen device 10 and/or the companion device 5 can be wirelessly synced between other devices such as a CGM device, a fitness tracker, or other user device operable to communicate with the device ecosystem connection module on the pen device 10 and/or the companion device 5.

In implementations of the device ecosystem connection module, for example, security credentials may be shared among devices as well, so that, for example, if the user replaces their companion device 5, he/she only needs to sync once with one device or a central server, and then all devices are given security credentials to communicate. Similarly, if an insulin pen device is replaced—connecting it to one device allows all of the user's devices to access it securely.

For example, when a patient transitions from an old pen device to a new one, the pens could communicate wirelessly or via a physical data cable to transfer information seamlessly for the user. This could include user preferences, clinical dosing data, the patient's medical parameters, prescription authorization, or security encryption keys, for example. Activating the new pen device could also be used to command the deactivation of the old one for security or safety purposes.

For example, multiple pens/caps/pumps have telemetry into a single system for a healthcare provider or clinical trial facilitator, so they can manage or monitor multiple users. Insulin devices may connect via Bluetooth to the end user's smart device, which then transfer data to a central server or host device. In some examples, the insulin injection devices may connect via Wi-Fi or cellular data to send data directly to a central server or the companion device 5.

In some examples, a smart insulin pen may have no display and no buttons or switches, meaning that a passcode cannot be entered or displayed. However, a secure connection and pairing between the correct pen and correct companion device are necessary.

In an example method, the device connection module can facilitate a device pairing between the pen device 10 and the companion device 5. For example, the user may dial a specific dose size on the pen device 10. The number would be secret and randomly generated for the companion device that it is to be connected to. In some implementations, multiple consecutive doses could be used in sequence to provide additional security. The method utilizes both the sizes and the timing of the dose dialing (e.g., including single or multiple doses) to identify the correct pen and prevent accidental or deliberate interception. In some implementations, the device pairing method can include a less-common action such a retraction or an arbitrary dose & retract sequence, which could be used to minimize accidental entering of the special sequence. The "secret" number entered to the pen could be used in two ways. In one example, the pen device 10 could confirm that the device attempting to connect knows the "secret" entry, allowing the pen device 10 to authenticate the device for the purposes of either bonding or telling the pen to debond itself from a previous device. In another example, the device could confirm that the pen knows the "secret" entry, allowing the device to authenticate the pen.

In some implementations, the pen device 10 could be actuated in close proximity or in physical contact with the companion device 5 (e.g., smartphone), and the smartphone's microphone could audibly detect exact dose timing (the overall start and end time, as well as very specific timing of each click) to identify the correct pen in a way that would be difficult to spoof. For example, in some implementations, the pen device 10 could have a unique ID that is either manually entered or photographed and automatically detected by the smartphone. For example, in some implementations, the pen device 10 could communicate via NFC to exchange a unique ID or secure passcode to the smartphone, to subsequently be used for Bluetooth or other wireless pairing security.

The companion device 5 (e.g., smartphone) is able to determine the signal strength (e.g., RSSI—received signal strength indicator, measured in dB) of the pen device 10, so this could also be used to identify the correct pen. If multiple pens are in range, the strongest RSSI could be selected for connection. To identify and authenticate a specific device, the user could be instructed to deliberately bring the pen close to or far from the device, so that it can confirm expected changes in RSSI.

Pump Transition/Coordination

In some implementations, the system is configured to interact with other medicine delivery systems such as pumps, e.g., insulin pumps.

In an example, prior to starting a treatment therapy using a pump device, a patient could use a smart pen (e.g., pen device 10) for a defined time period to determine the appropriate dosing regimen and/or clinical parameters (such as carb factor) for use with the pump. In another example, prior to moving from a pump device to a smart pen device for medicine treatment/therapy, i.e., transition from a pump to the pen device 10, the learning dose calculator module 220 (e.g., or an artificial pancreas module) could automatically receive settings, parameters, and dose history from the pump to allow for a seamless transition to the pen, with correct IOB and insulin calculation settings. For example, long-acting insulin doses can be calculated based on the pump's basal rate. For example, fast acting insulin doses can be calculated based on the pump's dose calculator settings, such as duration of insulin action and carb factor.

In some situations, for example, patient users like to take "pump holidays" where they take a break from wearing their pump. Pumps can be uncomfortable and/or restricting of certain activities. As such, the smart pen and smart dosing algorithm described herein can make this transition seamless, basing the pen therapy on the pump parameters, and vice versa. For example, tracking the long-acting (basal) insulin taken from a pen would allow the pump to automatically take over basal insulin dispensing at the right time when the long-acting insulin from a pen wears off. For example, if the same dose calculator (e.g., such as a dose calculator smartphone app) were used for the pump and pens, the user would have less to learn and manually keep track of when switching between the two. For example, if the dose calculator was aware of insulin from all pens and pumps, it could accurately track IOB and inform a closed loop (e.g., artificial pancreas) system to recommend correct dosing without losing control through the transition.

"Temporary Pump" Applications

There are times when a pen is not practical or desirable, e.g., such as during sleep, a workout, or certain social and work situations. However, many people still do not want to be continually attached to a pump. Currently patients must choose between the two, but a pump designed for temporary intermittent use could provide the best of both worlds, e.g., freedom from attachments when desired, and freedom from distractions when desired.

If a smart pen (or multiple pens, such as for long acting and fast acting insulin) and a temporary pump shared information and were aware of all insulin delivered, they could work in concert with a dose calculator, e.g., such as the learning dose calculator module 220 described herein, or AP algorithm to maintain glucose levels as the user switches between the devices. Notably, many existing conventional pumps have a replaceable infusion set (detachable tubing connected to a needle and/or adhesive patch) to allow reuse, however self-contained "patch pumps" are typically disposable with a permanently attached needle and adhesive patch. A self-contained pump (with no external tubing) could also be fitted with replaceable adhesive and/or a replaceable needle to facilitate the temporary-use application.

In such example applications, the patient user can manually indicate that they are about to remove the pump, and it could give one final bolus if needed (rather than continuing to dispense slowly), e.g., to reduce the need for an injection soon after. The pump may provide only meal and glucose correction insulin, relying on long-acting insulin to maintain basal. The pump could automatically take over for long-acting basal insulin when an existing dose wears off. Upon pump removal, it would prompt the user to take a long-acting pen dose to maintain basal insulin. The pen and pump could be the same device, designed to either administer a single dose while manually held against the skin, or a slow continuous flow when attached to the body. If the single device contained long and fast acting insulin, it could further reduce the number of injections required, administering a long-acting dose prior to "pump" removal, or simultaneously with a fast-acting correction dose.

Smart Cap

In some embodiments of the pen device 10, the pen device 10 includes a smart cap or carrying case that can act as a data relay from the pen to a wireless device, e.g., the companion device 5. In this way, the pen itself could have very low power and miniaturized electronics with a small power source, and the cap or case could have a larger battery (possibly rechargeable) that would handle the more power-intensive communication via Bluetooth or other similar protocol to a phone. The cap or case could connect wirelessly or via direct electrical contact with the pen.

Noise Filtering & Error Correcting Encoder

Rotary encoders are well-known in device design when a rotational motion needs to be sensed electrically. Typical rotary encoders have 2 channels with a quadrature output pattern, with two digital output channels that may each be in one of two states: "high" or "low", also referred to as "0" or "1". As they rotate, the two outputs alternate in sequence: 00, 01, 11, 10, 00, and so on as the shaft is rotated. In this way, relative position and direction of movement can be measured. The opposite sequence 00, 10, 11, 01, 00 would represent reverse rotation.

For some applications, optical encoders are used for high precision and high reliability. However, optical encoders constantly consume power, so for a battery-powered handheld device, such as a smart insulin pen measuring rotation of a dose dispensing mechanism, a mechanical encoder is desirable to minimize power consumption.

However, mechanical encoders have some limitations. Generally, precision (e.g., resolution) of mechanical encoders is much lower than optical encoders, which typically is due to practical limits of feature size and tolerance for the desired device. Or, said another way, high resolution mechanical encoders are more sensitive to alignment and tolerance, which affects signal quality. Edge transitions of mechanical encoders may be noisy or erratic, especially if rotation ends right on an edge. For this reason, typical rotary encoders must start and end in well-defined locations away from edge transitions. This requires alignment between physical detents and electrical positions. Furthermore, wear of the contact areas can affect the contact patch width, further affecting alignment and tolerancing. Moreover, corrosion and particulate (e.g., generated from wear or from ingressing from external sources, such as dust or lint) can cause erratic noise and poor contact.

Debouncing, i.e. adding a digital delay or analog RC circuit to smooth out the output, is often used to filter noise from encoders, but this is only useful if the noise is minimal and brief. Notably, any quadrature encoder is presumed to move in order, such that an instantaneous jump from 00 to 11 state is not defined, even though this could be detected due to erratic noise, poor contact alignment, or rotating the encoder more quickly than the controller can process.

To overcome these limitations of mechanical encoders, in particular for applications of a mechanical encoder in a handheld medicine injection pen such as the pen device 10, the present technology includes a noise filtering and error correcting method.

Implementations of the noise filtering and error correcting method can be used to address and overcome the following constraints, which typically exist for specific applications of mechanical encoders in medicine injection pens. For example, accurately measuring doses is critical, but accurately measuring retraction is not. It is relatively safe to misinterpret a retraction as a dose, but unsafe to misinterpret a dose as a retraction. For example, under-reporting the amount of insulin delivered to the user could lead them to subsequently overdose, but over-reporting would not. So in case of ambiguity, there is reason to err on the side of assuming a reading is a dose.

In a mechanical encoder with spring contacts sensing contact with a conductive pattern, any noise caused by particulate or corrosion will only cause poor contact—the signal will still be clean when an input line is disconnected. So, a noisy input signal can be assumed to indicate contact. An insulin pen will not randomly rotate in alternating directions the way other applications for rotary encoders (i.e., a volume knob) might, so any continuous stream of input can be assumed to indicate a single movement in one direction. And again, in case of ambiguity, it is safest to assume the movement is in the dosing direction. So if one state is skipped (e.g., such as transitioning from 00 to 11) it can safely be assumed that the encoder moved 2 steps in the direction it had been moving.

An insulin pen does not require instantaneous interpretation of each encoder edge. Doses are discrete events that include multiple edges that may be summed and interpreted after the entire movement is complete, e.g., after some timeout period when no further input is received).

Rotation in one direction may physically be able to move much faster than in the other direction. For example, an insulin pen can be dosed very quickly by pressing the button, but retracted much more slowly by manually turning the screw. In this case, any motion that is too fast to be processed in order (appearing as a simultaneous transition of both encoder channels—typically considered an invalid transition for a quadrature encoder) can be assumed to represent 2 steps in the forward direction.

The example noise filtering and error correcting method can be implemented to accurately read dose size from a mechanical encoder.

Figure 7:
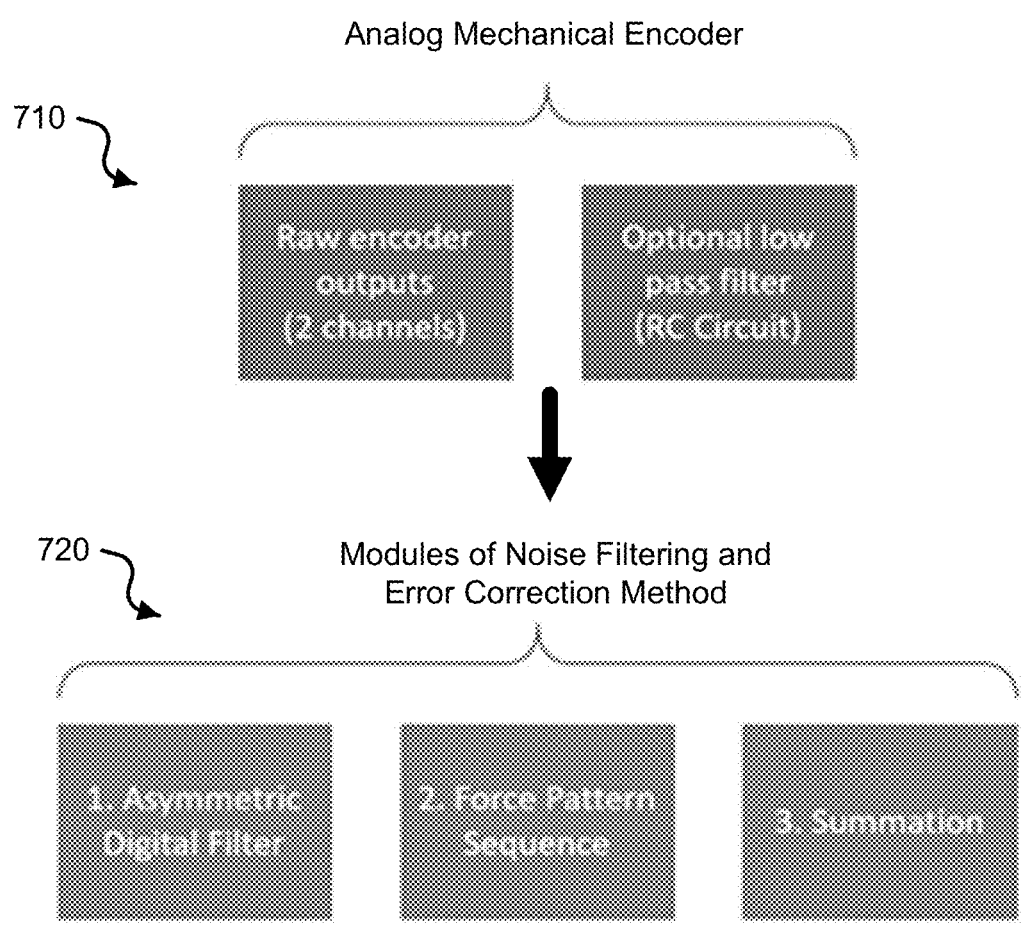
FIG. 7 shows a diagram depicting an example embodiment of a method for noise filtering and error correcting implementable by a mechanical encoder in an injection device.

FIG. 7 shows a diagram showing example processes of a noise filtering and error correcting method, which can be applied to the output signals of mechanical encoders, e.g., analog hardware. The diagram, at 710 of FIG. 7, shows an example of analog hardware that is typical for mechanical rotary encoders. The method can be implemented in software as part of the app on the companion device 5 or by a processor of the pen device 10. The diagram, at 720 of FIG. 7, depicts software modules of the noise filtering and error correction method that can be implemented to accurately measure doses, such as doses set and/or dispensed by the pen device 10.

The example noise filtering and error correcting method can receive the output signals of the analog mechanical encoder at one or both of modules 1 and 2, i.e., an asymmetric digital filter module (module 1) and a force pattern sequence module (module 2), respectively. Modules 1 and 2 are independent, and one may be implemented without the other. In the diagrams here, "low" is considered to be connected or "1", and "high" is considered disconnected or "0". For example, this is the case for an encoder where the input lines have pull-up resistors and the conductive encoder pattern is connected to ground.

Asymmetric Digital Filter

Execution of the module 1, the asymmetric digital filter module, can include the following. The output signals from the mechanical encoder can be received at the asymmetric digital filter module. FIG. 8A shows an example diagram showing two encoder channels (Channel A and Channel B), both before and after the implementation of the asymmetric digital filtering process of the method by the asymmetric digital filter module.

As shown in FIG. 8A, periods of noise are considered to indicate low, or connected. Only after a certain debounce time period of stable high signal is the line considered to indicate a high output. By this process, even periods of ambiguous erratic noise are correctly interpreted as indicating contact. When a signal is observed to drop from high to low state, it is automatically considered to be low regardless of noise.

For example, debouncing always introduces phase shift (i.e., a rising edge will not actually register as "high" until the debounce time has passed). Even though a falling edge is not debounced here, in this example, it must be delayed by the debounce time to prevent introducing phase error. This effect may be negligible in some applications, but otherwise it should be accounted for.

Force Pattern Sequence

Execution of the module 2, the force pattern sequence module, can include the following. The output signals from the asymmetric digital filter module can provide the input signals to the force pattern sequence module. In some implementations, the output signals from the mechanical encoder can be received at the force pattern sequence module. FIG. 8B shows an example diagram showing two encoder channels (Channel A and Channel B), both before and after the implementation of the force pattern sequence process of the method by the force pattern sequence module.

Typically with a quadrature encoder, any sequence of edges are considered to be true, even if they indicate alternating directions. However, in an insulin pen, for example, it is known that a single movement is all in the same direction, so we can assume this regardless of the input pattern. In cases of noise or contact wear, the signal could appear to be misaligned, but it is important that it is not misinterpreted as alternating directions of rotation.

Until the final summation, the method assumes forward motion. In the example shown in FIG. 8B, both channels are assumed at rest low and the next pattern in the forward sequence would be channel A rising.

Because channel B rises first, it is noted as an out-of-order edge (marked with an asterisk * in the diagram) but otherwise ignored and not counted until channel A rises. In this way, the algorithm is "forcing" the order of the edges to conform to the presumed forward direction of movement.

Summation

After a discrete movement is completed and no further input is received for some timeout period, it can be assumed that the dose is complete, and the sequence can be post-processed.

Execution of the module 3, the summation module, can include the following. The output signals from the force pattern sequence module can be received at the summation module. FIG. 8C shows an example diagram showing the two processed channels (Channel A and Channel B), before and after the implementation of the summation process of the method by the summation module.

For example, because 4 of the 5 edges were in the correct forward order, it can be inferred that the whole dose was in fact in the forward direction, and the 1 out-of-order was simply an error. If the movement had actually been in the reverse direction, every other edge would have been marked as out-of-order. If there were never phase errors, for example, it could be assumed that 0 out-of-order means forward, and half the edges out-of-order means reverse. Anywhere between these values indicates some phase error that we want to correct. In practice, a useful threshold is approximately 40%, for example. So if fewer than 40% of edges are marked as out-of-order, it is assumed that the dose was actually forward.

This is also useful for fault detection. Anything other than the exact 0% or 50% values indicates some signal error, so this can be measured by firmware to report malfunction or disable a defective device if multiple errors are registered over time.

Figure 8D:
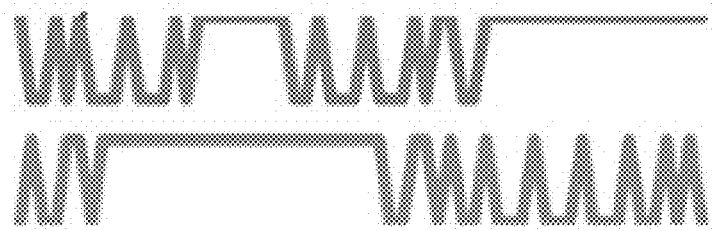

The diagrams shown in FIGS. 8A-8C demonstrate the capability of implementing the method to take a typically unusable signal and reliably filter it and correct for errors to produce an accurate reading. FIG. 8D shows a summary.

Figure 9:
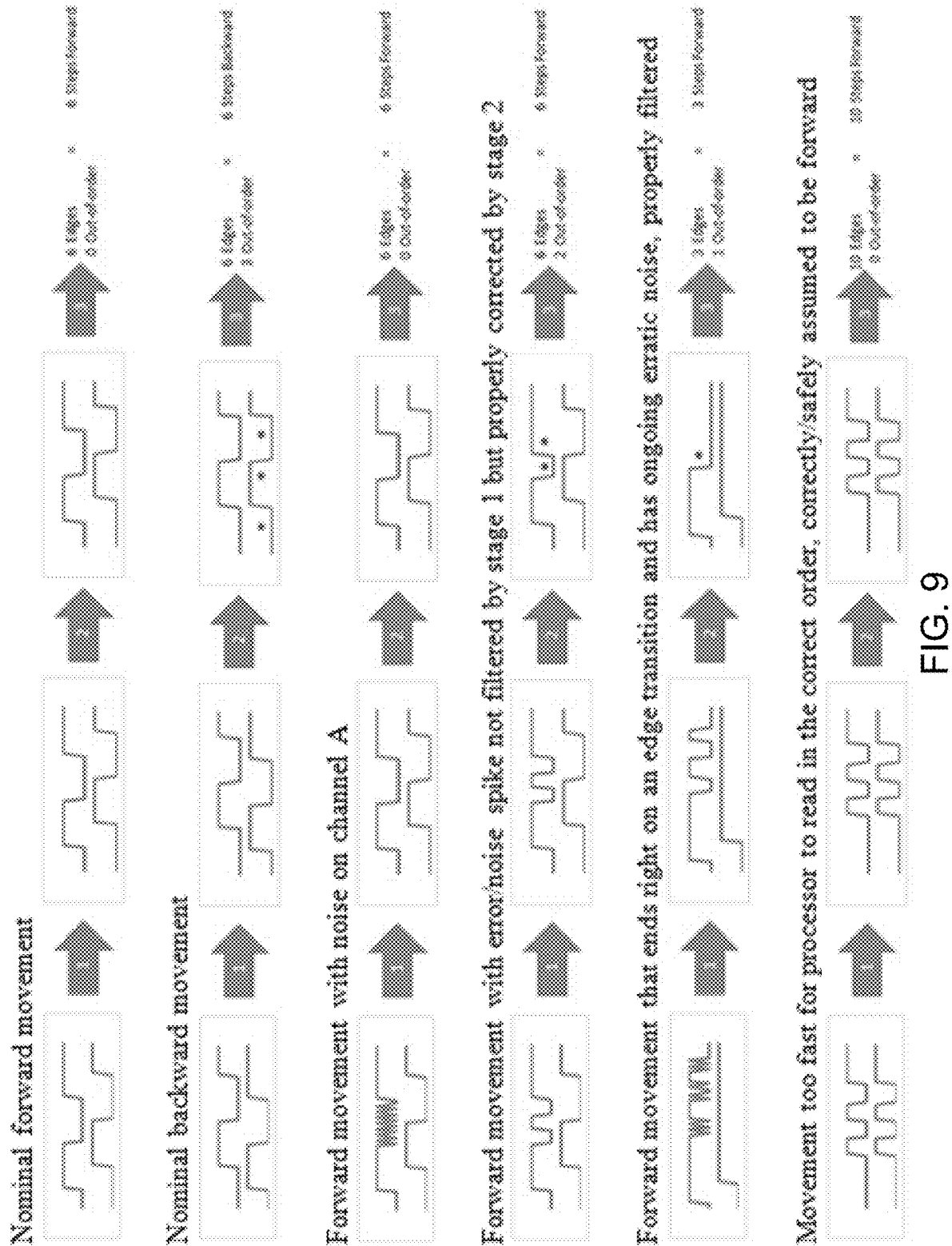
FIG. 9 shows plots depicting further example implementations of the noise filtering and error correcting method of FIG. 7.

FIG. 9 shows more example implementations of the noise filtering and error correcting method for nominal forward movement; nominal backward movement; forward movement with noise on one channel, e.g., Channel A; forward movement with error/noise spike not filtered by stage 1 but properly corrected by stage 2; forward movement that ends right on an edge transition and has ongoing erratic noise, properly filtered; and movement too fast for processor to read in the correct order, correctly/safely assumed to be forward.

Encoder Resolution

In addition to implementations of the noise filtering and error correcting method described above, by implementing an encoder with 3× the resolution of the mechanical assembly (so 3 encoder edges per 1 mechanical increment), exact alignment of mechanical detents and encoder edges is not necessary.

Slight variability in encoder phase alignment and mechanism rotation angles (e.g., due to normal part tolerances) could lead to error in the number of edges detected—it may result in 1 too many or 1 too few. Similarly, if rotation happens to end exactly on an edge transition, that channel may be noisy and in an ambiguous state.

If encoder resolution exactly matched the mechanism resolution 1 to 1, the cases above would result in error.

If encoder resolution was 2× that of the mechanism, it still leaves ambiguity. When 3 edges are detected, it is not clear whether that indicates 1 or 2 mechanical increments. And if 1 edge is detected, it is not clear whether that indicates 1 mechanical increment, or simply noise on that channel.

With at least 3× resolution, there is no ambiguity. 2-4 edges indicate 1 increment, 5-7 edges indicate 2 increments and so on. Further, 1 edge alone can confidently be disregarded as noise.

So with this example arrangement, after the above noise-filtering and error-correcting algorithm counts edges and determines direction, the edge count is divided by 3 and rounded to the nearest integer to determine the actual dose size.

Figure 10:
FIG. 10 shows a plot depicting another example implementations of the noise filtering and error correcting method of FIG. 7.

FIG. 10 shows an example. In the initial example, the processed channel signal resulted in determining 5 steps forward. For example, 5÷3=1.667 which rounds to 2, indicating 2 increments unambiguously. In a half-unit pen (e.g., such as an insulin pen), where each increment is ½ unit, the determined result is 1 unit dose.

EXAMPLES

In some embodiments in accordance with the disclosed technology (example 1), a system for administering a medicine to a patient includes an injection pen device including a dose setting mechanism to set a dose of a medicine contained in a medicine cartridge that is to be dispensed by the injection pen device, a dispensing mechanism to dispense the medicine according to the set dose, and electronic circuits including a processor, a memory comprising instructions executable by the processor, and a wireless transmitter, the processor of the injection pen device configured to generate dose data associated with a dispensing event of a dose of the medicine dispensed from the injection pen device and time data associated with the dispensing event, and to wirelessly transmit the dose data; and a mobile communication device in wireless communication with the injection pen device, the mobile communication device including a data processing unit including a processor and memory to receive and process the dose data, wherein the mobile communication device includes a software application program product comprising a non-transitory computer-readable storage medium having instructions, which when executed by the processor of the data processing unit, cause the mobile communication device to determine a recommended dose based on health data and contextual data associated with a user of the injection pen device, the contextual data including one or more of physical activity data, location data, and nutrient data corresponding to a food, wherein the software application program product includes a data aggregator that obtains the health data and the contextual data, and a learning dose calculator that calculates the recommended dose of the medicine, wherein dose calculations by the learning dose calculator are adapted in accordance with data associated with time, location, activity, and food at a particular time and specific to the user of the injection pen device.

Example 2 includes the system of example 1, wherein the instructions, when executed by the processor of the data processing unit, cause the mobile communication device to: receive one or more analyte values associated with a health condition of the user to which the medicine is associated; receive the health data and the contextual data associated with the user; determine a set of dose calculator parameter settings specific to the user's current health state; calculate a medicine dose value using the selected parameter settings; and generate at least one of a displayable output or actuatable output based on the calculated medicine dose value.

Example 3 includes the system of example 2, wherein the instructions, when executed by the processor of the data processing unit, cause the mobile communication device to: analyze a physiological response to a dosing outcome of the medicine injected into the user by the injection pen device at a dose dispensed according to the calculated medicine dose value; produce a learned set of dose calculator parameter settings by processing (i) the analyzed physiological response to the dosing outcome with (ii) a past set of dose setting parameters and (iii) the one or more analyte values and the health data and the contextual data that correspond to the set of dosing parameters determined for the calculated medicine dose value corresponding to the dosing outcome; and store the learned set of dose parameters by one or both of (i) modifying one or more existing dose calculator parameter settings and (ii) adding one or more new dose calculator parameter settings.

Example 4 includes the system of example 3, wherein analysis of the physiological response to the dosing outcome includes generating a quantitative score including a time data associated with a resultant analyte level and degree to which the resultant analyte level is within a target analyte level range.

Example 5 includes the system of any of examples 2-4, wherein the received one or more analyte values and/or the received health data and contextual data are imported from another software application operable on the mobile communication device.

Example 6 includes the system of any of examples 2-5, wherein the displayable output includes the recommended dose and is configured to be displayed on one or both of the mobile communication device and the injection pen device.

Example 7 includes the system of any of examples 2-6, wherein the actuatable output includes executable code to cause the injection pen device to actuate an operation including one or more of automatically setting, at the dose setting mechanism, the dose of the medicine to the calculated medicine dose value; or generating an alert indicative of a medicine dispensing event at the calculated medicine dose value.

Example 8 includes the system of any of the preceding examples, wherein the software application is configured to continuously adaptively calculate the recommended dose of the medicine on a periodic or intermittent basis.

Example 9 includes the system of any of the preceding examples, wherein the software application includes a food identification module to process the contextual data associated with a food to eat or eaten by the user of the injection pen device and additional data including at least one of a food history, a location of the user, or a time of day to produce a data set that is processable by the learning dose calculator to calculate the recommended dose.

Example 10 includes the system of example 9, wherein instructions, when executed by the processor of the data processing unit, cause the mobile communication device to produce a food data parameter for dose calculation including meal nutritional content associated with the food to eat or eaten by the user, by: identifying information associated with a food item from an image of the food item and based on a current time and day and a current location, wherein the identified information associated with the food item includes a type of the food item and an estimated amount of carbohydrates in the food item; estimating a probability of food items based on the current time and day and the current location in conjunction with personal food history data specific to the user; and generating the food data parameter using at least one of the identified information associated with the food item or the estimated probability of food items.

Example 11 includes the system of example 10, wherein the identifying the information associated with the food item includes executing image recognition processing of the food item image based on the current time and day and the current location in conjunction with food history data.

Example 12 includes the system of example 10, wherein the food history data is specific to the user and includes a frequency of food items consumed at a location or locations proximate to the current location and at a time or times proximate to the current time and day.

Example 13 includes the system of example 10, wherein the food history data includes crowdsourced food history data obtained from other individuals, wherein the crowdsourced food history data is stored in a cloud database accessible by the software application on the mobile communication device.

Example 14 includes the system of example 13, wherein the crowdsourced food history data includes of individual physiological response data to specific medicine doses associated with consumption of specific food items for a plurality of individual users.

Example 15 includes the system of any of examples 10-14, wherein instructions, when executed by the processor of the data processing unit, cause the mobile communication device to: produce a prompt, displayable on the mobile communication device, to request a confirmation of the identified information associated with a food item, and/or produce a prompt, displayable on the mobile communication device, to request an input indicative of a user modification to the information.

Example 16 includes the system of example 10, wherein the estimated probability of food items includes a sorted list of the food items and their corresponding estimated probability values.

Example 17 includes the system of example 16, wherein instructions, when executed by the processor of the data processing unit, cause the mobile communication device to: produce a prompt, displayable on the mobile communication device, to request a selection of a particular food item on the sorted list.

Example 18 includes the system of any of the preceding examples, wherein the health data includes information pertaining to one or more of a previous dose of the medicine, or a measured analyte of the user.

Example 19 includes the system of any of the preceding examples, wherein the contextual data further includes information pertaining to one or more of a measured heart rate of the user, a measured blood pressure of the user, an event attended or to be attended by the user, or a mental state of the user.

Example 20 includes the system of any of the preceding examples, wherein the mobile communication device is implemented on a smartphone.

Example 21 includes the system of any of the preceding examples, wherein the mobile communications device is implemented on one or more of a tablet, a wearable computing device including a smartwatch or smartglasses, a computer including a laptop computer, or one or more computers networked in a communication network through the Internet.

Example 22 includes the system of any of the preceding examples, wherein the medicine includes a bolus insulin or a basal insulin.

In some embodiments in accordance with the disclosed technology (example 23), a method for determining a recommended dose of a medicine based on health data and contextual data associated with a user of a medicine injection pen device, the method comprising: receiving, at a computing device, one or more analyte values associated with a health condition of a user of the medicine injection pen device to which the medicine is associated; receiving, at the computing device, the health data and the contextual data associated with the user; determining, at the computing device, a set of dose calculator parameter settings specific to the user's current health state; calculating, at the computing device, a medicine dose value using the selected parameter settings; and generating, at the computing device, at least one of a displayable output or actuatable output based on the calculated medicine dose value, wherein the health data includes information pertaining to one or more of a previous dose of the medicine or a measured analyte of the user of the medicine injection pen device, and wherein the contextual data includes one or more of physical activity data, location data, and nutrient data corresponding to a food.

Example 24 includes the method of example 23, further comprising: analyzing, at the computing device, a physiological response to a dosing outcome of the medicine injected into the user by the injection pen device at a dose dispensed according to the calculated medicine dose value; producing, at the computing device, a learned set of dose calculator parameter settings by processing (i) the analyzed physiological response to the dosing outcome with (ii) a past set of dose setting parameters and (iii) the one or more analyte values and the health data and the contextual data that correspond to the set of dosing parameters determined for the calculated medicine dose value corresponding to the dosing outcome; and saving, by the computing device, the learned set of dose parameters by one or both of (i) modifying one or more existing dose calculator parameter settings and (ii) adding one or more new dose calculator parameter settings.

Example 25 includes the method of any of the preceding examples, wherein the computing device includes a smartphone.

Example 26 includes the method of any of the preceding examples, wherein the computing device includes one or more of a tablet, a wearable computing device including a smartwatch or smartglasses, a computer including a laptop computer, or one or more computers networked in a communication network through the Internet.

Example 27 includes the method of any of the preceding examples, wherein the medicine includes a bolus insulin or a basal insulin.

In some embodiments in accordance with the disclosed technology (example 28), a method for processing signals from a mechanical encoder of a medicine injection pen device, the method comprising: receiving analog output signals from the mechanical encoder, the mechanical encoder comprising at least two signal channels; applying an asymmetric digital filter to the received analog output signals to produce a set of filtered signals; and applying a force pattern sequence to the filtered signals to resolve an out-of-order edge on one of the at least two channels to produce a set of noise-filtered and error-corrected encoder signals, wherein the produced noise-filtered and error-corrected encoder signals are associated with a dose setting of the medicine injection pen device.

Example 29 includes the method of example 28, wherein the applying the asymmetric digital filter includes converting a range of fluctuating signals within a time period of the analog output signals as a connected signal or a disconnected signal within the time period based on predetermined debounce time criteria.

Example 30 includes the method of example 29, wherein the disconnected signal corresponds to a relatively longer debounce time than a connected signal.

Example 31 includes the method of any of examples 28-30, wherein the applying the force pattern sequence includes converting a portion of the analog output signal on a channel that corresponds to the out-of-order edge as a disconnected signal.

Example 32 includes the method of example 31, wherein the out-of-order edge is converted to conform to a predetermined motion direction of the mechanical encoder.

Example 33 includes the method of any of the preceding examples, further comprising: post-processing the set of noise-filtered and error-corrected encoder signals from the applied force pattern sequence process to determine a number of steps and direction of actuation of the mechanical encoder.

Example 34 includes the method of any of the preceding examples, comprising: calculating a dose setting from the medicine injection pen device comprising the mechanical encoder from the output signals of the mechanical encoder.

Example 35 includes the method of example 34, wherein the calculated dose setting includes units associated with the medicine of the injection pen device.

In some embodiments in accordance with the disclosed technology (example 36), a system for administering a medicine to a patient includes an injection pen device including a dose setting mechanism to set a dose of a medicine contained in a medicine cartridge that is to be dispensed by the injection pen device, a dispensing mechanism to dispense the medicine according to the set dose, a mechanical encoder comprising at least two channels operable to produce analog output signals corresponding to a dose setting, and electronic circuits including a processor, a memory, and a wireless transmitter, the processor of the pen device configured to generate dose data associated with a dispensing event of a dose of the medicine dispensed from the injection pen device and time data associated with the dispensing event, and to wirelessly transmit the dose data; and a mobile communication device in wireless communication with the injection pen device, the mobile communication device including a data processing unit including a processor and memory to receive and process the dose data, wherein at least one of the injection pen device or the mobile communication device includes a software application program product comprising a non-transitory computer-readable storage medium having instructions, which when executed by the processor, cause the at least one of the injection pen device or the mobile communication device to process signals from the mechanical encoder by: applying an asymmetric digital filter to the analog output signals to produce a set of filtered signals, and applying a force pattern sequence to the filtered signals to resolve an out-of-order edge on one of the at least two channels to produce a set of noise-filtered and error-corrected encoder signals.

Example 37 includes the system of example 36, wherein the applying the asymmetric digital filter includes converting a range of fluctuating signals within a time period of the analog output signals as a connected signal or a disconnected signal within the time period based on predetermined debounce time criteria.

Example 38 includes the system of example 37, wherein the disconnected signal corresponds to a relatively longer debounce time than a connected signal.

Example 39 includes the system of any of examples 36-38, wherein the applying the force pattern sequence includes converting a portion of the analog output signal on a channel that corresponds to the out-of-order edge as a disconnected signal.

Example 40 includes the system of example 39, wherein the out-of-order edge is converted to conform to a predetermined motion direction of the mechanical encoder.

Example 41 includes the system of any of the preceding examples, wherein the software application program product is configured to post-process the set of noise-filtered and error-corrected encoder signals from the applied force pattern sequence process to determine a number of steps and direction of actuation of the mechanical encoder.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A system for administering a medicine to a patient, comprising:
   an injection pen device including a dose setting mechanism to set a dose of a medicine contained in a medicine cartridge that is to be dispensed by the injection pen device, a dispensing mechanism to dispense the medicine according to the set dose, and electronic circuits including a processor, a memory storing instructions executable by the processor, and a wireless transmitter, the processor of the injection pen device configured to generate dose data associated with a dispensing event of a dose of the medicine dispensed from the injection pen device and time data associated with the dispensing event, and to wirelessly transmit the dose data;
   a mobile communication device in wireless communication with the injection pen device, the mobile communication device including a data processing unit including a processor and a memory to receive and process the dose data, wherein the mobile communication device includes a non-transitory computer-readable storage medium having instructions, which when executed by the processor of the data processing unit, cause the mobile communication device to determine a recommended dose based on health data and contextual data associated with a user of the injection pen device, the contextual data including one or more of physical activity data, location data, or nutrient data corresponding to a food,
   wherein the memory of the mobile communication device stores a data aggregator that obtains the health data and the contextual data, and a learning dose calculator that calculates the recommended dose of the medicine, wherein dose calculations by the learning dose calculator are adapted in accordance with data associated with time, location, activity, and food at a particular time and specific to the user of the injection pen device; and
   an encoder disposed within the injection pen device and in communication with the processor of the injection pen device, the encoder configured to generate an analog output signal in response to movement of the dispensing mechanism to dispense the medicine, wherein at least one of the memory of the injection pen device or the memory of the mobile communication device stores a digital noise filter module configured to apply an algorithm that forces at least one edge of the analog output signal of the encoder to conform to a pattern consistent with a forward direction of movement to determine a quantity of the dose of the medicine dispensed from the injection pen device.

2. The system of claim 1, wherein the instructions, when executed by the processor of the data processing unit, cause the mobile communication device to:
   receive one or more analyte values associated with a health condition of the user to which the medicine is associated;
   receive the health data and the contextual data associated with the user;
   determine a set of dose calculator parameter settings specific to a current health state of the user;
   calculate a medicine dose value using the set of dose calculator parameter settings; and
   generate at least one of a displayable output or actuatable output based on the calculated medicine dose value.

3. The system of claim 2, wherein the instructions, when executed by the processor of the data processing unit, cause the mobile communication device to:
   produce a learned set of dose calculator parameter settings by processing (i) a physiological response of the user to an injection of the medicine into the user at a dose dispensed according to the medicine dose value with (ii) a past set of dose calculator parameter settings and (iii) the one or more analyte values and the health data and the contextual data that correspond to the set of dose calculator parameter settings determined for the calculated medicine dose value corresponding to the injection of the medicine into the user; and
   store the learned set of dose calculator parameter settings by one or both of (i) modifying one or more existing dose calculator parameter settings and (ii) adding one or more new dose calculator parameter settings.

4. The system of claim 3, wherein the instructions, when executed by the processor of the data processing unit, cause the mobile communication device to generate a quantitative score associated with the physiological response of the user including time data associated with a resultant analyte level and degree to which the resultant analyte level is within a target analyte level range.

5. The system of claim 2, wherein the received one or more analyte values and/or the received health data and contextual data are imported from a software application operable on the mobile communication device.

6. The system of claim 2, wherein the displayable output includes the recommended dose and is configured to be displayed on one or both of the mobile communication device and the injection pen device.

7. The system of claim 2, wherein the actuatable output includes executable code to cause the injection pen device to actuate an operation including one or more of automatically setting, at the dose setting mechanism, the dose of the medicine to the calculated medicine dose value; or generating an alert indicative of a medicine dispensing event at the calculated medicine dose value.

8. The system of claim 1, wherein the instructions, when executed by the processor of the data processing unit, cause the mobile communication device to update the recommended dose of the medicine on one of a periodic basis, a continuous basis, or an intermittent basis.

9. The system of claim 1, wherein the memory of the mobile communication device stores a food identification module to process the contextual data associated with a food to eat or eaten by the user of the injection pen device and additional data including at least one of a food history, a location of the user, or a time of day to produce a data set that is processable by the learning dose calculator to calculate the recommended dose.

10. The system of claim 9, wherein the instructions, when executed by the processor of the data processing unit, cause the mobile communication device to produce a food data parameter for dose calculation including meal nutritional content associated with the food to eat or eaten by the user, by:
   identifying information associated with a food item from an image of the food item and based on a current time and day and a current location, wherein the identified information associated with the food item includes a type of the food item and an estimated amount of carbohydrates in the food item;

estimating a probability of food items based on the current time and day and the current location in conjunction with personal food history data specific to the user; and generating the food data parameter using at least one of the identified information associated with the food item or the estimated probability of food items.

11. The system of claim 10, wherein the identifying the information associated with the food item includes executing image recognition processing of the food item image based on the current time and day and the current location in conjunction with food history data.

12. The system of claim 10, wherein the food history data is specific to the user and includes a frequency of food items consumed at a location or locations proximate to the current location and at a time or times proximate to the current time and day.

13. The system of claim 10, wherein the food history data includes crowdsourced food history data obtained from other individuals, wherein the crowdsourced food history data is stored in a cloud database accessible by the mobile communication device.

14. The system of claim 13, wherein the crowdsourced food history data includes of individual physiological response data to specific medicine doses associated with consumption of specific food items for a plurality of individual users.

15. The system of claim 10, wherein the instructions, when executed by the processor of the data processing unit, cause the mobile communication device to:

produce a prompt, displayable on the mobile communication device, to request a confirmation of the identified information associated with a food item, and/or produce a prompt, displayable on the mobile communication device, to request an input indicative of a user modification to the information.

16. The system of claim 10, wherein the estimated probability of food items includes a sorted list of the food items and their corresponding estimated probability values.

17. The system of claim 1, wherein the health data includes information pertaining to one or more of a previous dose of the medicine, or a measured analyte of the user.

18. The system of claim 1, wherein the contextual data further includes information pertaining to one or more of a measured heart rate of the user, a measured blood pressure of the user, an event attended or to be attended by the user, or a mental state of the user.

19. The system of claim 1, wherein the mobile communications device is implemented on one or more of a tablet, a wearable computing device including a smartwatch or smartglasses, a computer including a laptop computer, or one or more computers networked in a communication network through the Internet.

20. A system for administering a medicine to a patient, comprising:

an injection pen device including:
a dispensing mechanism movable within the injection pen device to dispense medicine;
a processor and a memory storing instructions executable by the processor to generate data associated with dispensing of the medicine from the injection pen device; and
a wireless transmitter configured to wirelessly transmit the data generated by the processor;

an encoder disposed within the injection pen device and in communication with the processor of the injection pen device, the encoder configured to generate an analog output signal in response to movement of the dispensing mechanism to dispense the medicine; and a mobile communication device in wireless communication with the injection pen device, the mobile communication device including a processor and a memory storing instructions executable by the processor of the mobile communication device, wherein at least one of the memory of the injection pen device or the memory of the mobile communication device stores a digital noise filter module configured to apply an algorithm that forces at least one edge of the analog output signal generated by the encoder to conform to a pattern consistent with a forward direction of movement to determine a quantity of the dose of the medicine dispensed from the injection pen device.

\* \* \* \* \*